US008623354B2

(12) United States Patent
Brown et al.

(10) Patent No.: US 8,623,354 B2
(45) Date of Patent: Jan. 7, 2014

(54) THERAPEUTIC COMPOSITIONS COMPRISING HYALURONAN AND THERAPEUTIC ANTIBODIES AS WELL AS METHODS OF TREATMENT

(75) Inventors: Tracey J. Brown, Flemington (AU); Gary R. Brownlee, East Burwood (AU)

(73) Assignee: Alchemia Oncology Pty Limited, Eight Mile Plains (AU)

( * ) Notice: Subject to any disclaimer, the term of this patent is extended or adjusted under 35 U.S.C. 154(b) by 863 days.

(21) Appl. No.: 12/065,945

(22) PCT Filed: Sep. 4, 2006

(86) PCT No.: PCT/AU2006/001293
§ 371 (c)(1),
(2), (4) Date: Sep. 29, 2008

(87) PCT Pub. No.: WO2007/028196
PCT Pub. Date: Mar. 15, 2007

(65) Prior Publication Data
US 2009/0220497 A1    Sep. 3, 2009

Related U.S. Application Data

(60) Provisional application No. 60/715,293, filed on Sep. 7, 2005, provisional application No. 60/788,589, filed on Mar. 31, 2006.

(51) Int. Cl.
*A61K 39/395* (2006.01)
*C07K 16/00* (2006.01)
*C07K 16/46* (2006.01)

(52) U.S. Cl.
USPC ............... 424/130.1; 424/133.1; 424/143.1; 424/155.1; 424/156.1; 530/387.1; 530/387.3; 530/388.22

(58) Field of Classification Search
None
See application file for complete search history.

(56) References Cited

U.S. PATENT DOCUMENTS

| | | |
|---|---|---|
| 4,141,973 A | 2/1979 | Balazs |
| 4,160,452 A | 7/1979 | Theeuwes |
| 4,256,108 A | 3/1981 | Theeuwes |
| 4,265,874 A | 5/1981 | Bonsen et al. |
| 4,522,811 A | 6/1985 | Eppstein et al. |
| 4,665,107 A | 5/1987 | Micale |
| 4,736,024 A | 4/1988 | Della Valle et al. |
| 4,851,521 A | 7/1989 | della Valle et al. |
| 4,965,353 A | 10/1990 | della Valle et al. |
| 5,095,037 A | 3/1992 | Iwamitsu et al. |
| 5,128,450 A | 7/1992 | Urdal et al. |
| 5,202,431 A | 4/1993 | della Valle et al. |
| 5,208,020 A | 5/1993 | Chari et al. |
| 5,284,656 A | 2/1994 | Platz et al. |
| 5,416,071 A | 5/1995 | Igari et al. |
| 5,442,053 A | 8/1995 | Della Valle et al. |
| 5,475,092 A | 12/1995 | Chari et al. |
| 5,585,499 A | 12/1996 | Chari et al. |
| 5,662,895 A | 9/1997 | Welte et al. |
| 5,676,964 A | 10/1997 | Della Valle et al. |
| 5,733,891 A | 3/1998 | Akima et al. |
| 5,744,155 A | 4/1998 | Friedman et al. |
| 5,756,475 A | 5/1998 | Inomata et al. |
| 5,756,537 A | 5/1998 | Gill |
| 5,776,925 A | 7/1998 | Young et al. |
| 5,827,834 A | 10/1998 | Falk et al. |
| 5,830,882 A | 11/1998 | Falk et al. |
| 5,840,673 A | 11/1998 | Buckbinder et al. |
| 5,846,545 A | 12/1998 | Chari et al. |
| 5,847,002 A | 12/1998 | Willoughby et al. |
| 5,852,002 A | 12/1998 | Falk et al. |
| 5,968,972 A | 10/1999 | Broder et al. |
| 5,977,088 A | 11/1999 | Harper et al. |
| 5,985,850 A | 11/1999 | Falk et al. |
| 5,985,851 A | 11/1999 | Falk et al. |
| 6,027,741 A | 2/2000 | Cialdi et al. |
| 6,069,135 A | 5/2000 | Falk et al. |
| 6,087,350 A | 7/2000 | Johnson et al. |
| 6,214,860 B1 | 4/2001 | Sola et al. |
| 6,232,301 B1 | 5/2001 | Takahashi et al. |
| 6,242,457 B1 | 6/2001 | Penco et al. |
| 6,299,900 B1 | 10/2001 | Reed et al. |
| 6,475,795 B1 | 11/2002 | Turley et al. |
| 6,552,184 B1 | 4/2003 | Pallado et al. |
| 6,579,978 B1 | 6/2003 | Renier et al. |
| 6,620,927 B2 | 9/2003 | Bulpitt et al. |
| 6,831,172 B1 | 12/2004 | Barbucci et al. |
| 7,420,033 B2 | 9/2008 | Varadhachary et al. |
| 2002/0015724 A1 | 2/2002 | Yang et al. |
| 2003/0087877 A1* | 5/2003 | Calias et al. .................... 514/54 |
| 2003/0180382 A1 | 9/2003 | Brown et al. |
| 2005/0042303 A1 | 2/2005 | Brown et al. |

(Continued)

FOREIGN PATENT DOCUMENTS

| | | |
|---|---|---|
| CA | 612307 A | 1/1961 |
| CA | 1227427 A1 | 9/1987 |

(Continued)

OTHER PUBLICATIONS

Cunningham et al. Cetuximab Monotherapy and Cetuximab plus Irinotecan in Irinotecan-Refractory Metastatic Colorectal Cancer. N. Engl J Med 2004;351:337-45.*

(Continued)

*Primary Examiner* — Maher Haddad
(74) *Attorney, Agent, or Firm* — Morrison & Foerster LLP

(57) ABSTRACT

The present invention relates generally to treatment and prophylactic protocols for cellular diseases or disorders, such as diseases and disorders associated with abnormal cellular proliferation. More particularly, the present invention provides compositions comprising therapeutic antibodies and hyaluronan and their use in the treatment or prophylaxis of cellular diseases and disorders.

14 Claims, 10 Drawing Sheets

(56) References Cited

U.S. PATENT DOCUMENTS

| | | | |
|---|---|---|---|
| 2005/0267069 | A1 | 12/2005 | Brown et al. |
| 2006/0178342 | A1 | 8/2006 | Brown et al. |
| 2006/0263395 | A1 | 11/2006 | Brown et al. |
| 2007/0148734 | A1* | 6/2007 | Chaudhuri et al. ........ 435/69.1 |
| 2008/0063727 | A1* | 3/2008 | Kim et al. ................. 424/499 |
| 2009/0054537 | A1 | 2/2009 | Brown |
| 2009/0306012 | A1 | 12/2009 | Brown et al. |

FOREIGN PATENT DOCUMENTS

| | | |
|---|---|---|
| CA | 2089621 A1 | 8/1994 |
| CA | 2122519 A1 | 10/1995 |
| CA | 2208924 A | 1/1999 |
| CA | 2370003 A1 | 7/2000 |
| CA | 2 387 058 A1 | 4/2001 |
| CA | 2 387 058 C | 4/2001 |
| EP | 0 138 572 B1 | 4/1985 |
| EP | 0 216 453 A2 | 4/1987 |
| EP | 0 216 453 A3 | 4/1987 |
| EP | 0 216 453 B1 | 4/1987 |
| EP | 0 265 116 B1 | 4/1988 |
| EP | 0 341 745 A1 | 11/1989 |
| EP | 0 341 745 B1 | 11/1989 |
| EP | 0 433 817 B1 | 6/1991 |
| EP | 0 626 863 B1 | 12/1994 |
| EP | 1 598 371 A1 | 11/2005 |
| JP | 61-000017 A | 1/1986 |
| JP | 61-91986 U | 6/1986 |
| JP | 4-504579 A | 8/1992 |
| JP | 2002-534484 A | 10/2002 |
| JP | 2003-518510 A | 6/2003 |
| WO | WO-91/04058 A2 | 4/1991 |
| WO | WO-93/16733 A1 | 9/1993 |
| WO | WO-94/15640 A1 | 7/1994 |
| WO | WO-94/23725 A1 | 10/1994 |
| WO | WO-95/30423 A2 | 11/1995 |
| WO | WO-95/30423 A3 | 11/1995 |
| WO | WO-95/30439 A2 | 11/1995 |
| WO | WO-95/30439 A3 | 11/1995 |
| WO | WO-96/06622 A1 | 3/1996 |
| WO | WO-97/20564 A1 | 6/1997 |
| WO | WO-97/40841 A1 | 11/1997 |
| WO | WO-98/17320 A1 | 4/1998 |
| WO | WO-98/23648 A1 | 6/1998 |
| WO | WO-99/02151 A1 | 1/1999 |
| WO | WO-00/20642 A1 | 4/2000 |
| WO | WO-00/41730 A1 | 7/2000 |
| WO | WO-01/36656 A2 | 5/2001 |
| WO | WO-01/47561 A1 | 7/2001 |
| WO | WO-02/05852 A1 | 1/2002 |
| WO | WO-02/090390 A1 | 11/2002 |
| WO | WO-03/018062 A1 | 3/2003 |
| WO | WO-2004/076491 A1 | 9/2004 |
| WO | WO-2006/107124 A1 | 10/2006 |
| WO | WO-2007/012133 A1 | 2/2007 |

OTHER PUBLICATIONS

Váradi et al. Binding of Trastuzumab to ErbB2 Is Inhibited by a High Pericellular Density of Hyaluronan. Journal of Histochemistry & Cytochemistry 60(8) 567-575.*

Varadi et al. Binding of Trastuzumab to ErbB2 is anhibited by a High Pericelluiar Density of Hyaluronan. J. Histochem Cytochem 60:567-575, 2012.*

Anonymous. (1957). "British Standard Methods for the Determination of the Viscosity of Liquids in C.G.S. Units," *British Standards Institution*, British Standards House, London, 4 pages.

Barrow, G.M. (1979). *Physical Chemistry, Fourth Edition*, Jackson, D.C. eds., McGraw-Hill Kogakusha, Ltd., Tokyo, Japan, pp. 764-765.

Final Office Action mailed Jun. 30, 2010, for U.S. Appl. No. 11/198,663, filed Aug. 5, 2005, 10 pages.

Wikipedia. (download on Sep. 13, 2010). "Intrinsic Viscosity," <http://en.wikipedia.org/wiki/Intrinsic_viscosity>, 3 pages.

Wikipedia. (download on Sep. 13, 2010). "Mark-Houwink Equation," <http://en.wikipedia.org/wiki/Mark%E2%80%93Houwink_equation>, 2 pages.

Wikipedia. (downloaded on Sep. 13, 2010). "Viscosity," located at <http://en.wikipedia.org/wiki/Viscosity>, 18 pages.

Zhen, Y. et al. (eds). (Nov. 2002). *Modern Biotechnological Pharmaceutics Series*, Antibody Engineering Pharmaceutics, Chemical Industry Press et al., Beijing, China, pp. 303-302, with Certified English Translation, for a total of 10 pages.

Bucci, L.R. et al. (2004). "Will the Real Hyaluronan Please Stand Up?" *Journal of Applied Nutrition* 54(1):10-33.

Final Office Action mailed Mar. 12, 2010, for U.S. Appl. No. 11/198,663, filed Aug. 5, 2005, 14 pages.

Non-Final Office Action mailed Mar. 25, 2010, for U.S. Appl. No. 09/889,203, filed Jan. 6, 2000, 11 pages.

Final Office Action mailed Apr. 30, 2010, for U.S. Appl. No. 11/415,612, filed May 1, 2006, 13 pages.

Avis, K.E. (1975). "Parenteral Preparations," Chapter 84 in *Remington's Pharmaceutical Sciences*, 15th Edition, Easton: Mack Publishing Company, pp. 1461-1487.

Deardorff, D.L. (1975). "Isotonic Solutions," Chapter 79 in *Remington's Pharmaceutical Sciences*, 15th Edition, Easton: Mack Publishing Company, pp. 1405-1412.

International Search Report mailed Oct. 17, 2006, for PCT Application No. PCT/AU2006/001293, filed Sep. 4, 2006, three pages.

Langer, R. (Sep. 28, 1990). "New Methods of Drug Delivery," *Science* 249:1527-1533.

Maucher, A. et al. (1994). "Antitumor Activity of Coumarin and 7-Hydroxycoumarin Against 7,12-dimethylbenz[$\alpha$]anthracene-Induced Rat Mammary Carcinomas," *J. Cancer Res. Clin. Oncol.* 120:502-504.

U.S. Appl. No. 09/889,203, filed Jan. 6, 2000, by Brown.

U.S. Appl. No. 12/482,870, filed Jun. 11, 2009, by Brown et al.

Bernatchez, S.F. et al. (1994). "Sodium Hyaluronate as a Vehicle for an Improved Tolerance of 5-Fluorouracil Administered Subconjunctivally to Rabbits," *International Journal of Pharmaceutics* 106:161-166.

Canadian Office Action mailed Apr. 15, 2009, for CA Application No. 2,458,856, two pages.

European Search Report mailed Sep. 26, 2005, for EP Application No. 01951219.3, four pages.

Final Office Action mailed Oct. 30, 2008, for U.S. Appl. No. 09/889,203, filed Mar. 13, 2002, 13 pages.

Final Office Action mailed May 11, 2009, for U.S. Appl. No. 11/191,407, filed Jul. 27, 2005, 12 pages.

International Search Report dated Jul. 22, 1994, for PCT Application No. PCT/CA94/00207, filed Apr. 15, 1994, three pages.

International Search Report mailed Apr. 14, 2000, for PCT Application No. PCT/AU00/00004, filed Jan. 6, 2000, six pages.

International Search Report mailed Aug. 22, 2001, for PCT Application No. PCT/AU01/00849, filed Jul. 13, 2001, three pages.

International Search Report mailed Oct. 14, 2002, for PCT Application No. PCT/AU02/01160, filed Aug. 27, 2002, three pages.

International Search Report mailed Sep. 22, 2006, for PCT Application No. PCT/AU2006/001059, filed Jul. 27, 2006, eight pages.

Izawa, O.N. et al. (May 11, 1992). "Hyaluronic Acid Derivative Synthesis and Properties (II)—Synthesis of Hyaluronic Acid Derivative with Thymine 5FU," *41$^{st}$ Society of Polymer Science Japan Conference Proceedings, Polymer Preprints*, Japan, May 26-29, 1992, 42(3):479. (with English translation, eight pages.)

Japanese Office Action mailed Jul. 7, 2009, for JP Application No. 2003-522577, with English translation, five pages.

Klein, E.S. et al. (1994). "Effects of Hyaluronic Acid on Experimental Tumor Uptake of 5-Flurouracil," *Reg. Cancer Treat.* 7:163-164.

Luo, Y. et al. (1999, e-pub. Jul. 27, 1999). "Synthesis and Selective Cytotoxicity of Hyaluronic Acid-Antitumor Bioconjugate," *Bioconjugate Chemistry* 10:755-763.

Non-Final Office Action mailed May 14, 2009, for U.S. Appl. No. 11/415,612, filed May 1, 2006, four pages.

Non-Final Office Action mailed Jun. 11, 2009, for U.S. Appl. No. 11/198,663, filed Aug. 5, 2005, 14 pages.

(56) References Cited

OTHER PUBLICATIONS

Ouchi, T. et al. (1991). "Design of Polysaccharide-5-Fluorouracil Conjugates Exhibiting Antitumour Activities," Chapter 8 *In American Chemical Society Symposium Series*, 469(Polymeric Drugs and Drug Delivery Systems):71-83.

Reynolds, J.E.F. ed. (1993). *Martindale: The Extra Pharmacopoeia*, 30th Edition, The Pharmaceutical Press: London, England, pp. 480-482.

Rivory, L.P. et al. (1996). "Conversion of Irinotecan (CPT-11) to Its Active Metabolite, 7-Ethyl-10-hydroxycamptothecin (SN-38), by Human Liver Carboxylesterase," *Biochemical Pharmacology* 52:1103-1111.

Rosenthal, M.A. et al. (2005, e-pub. May 9, 2005). "Phase I and Pharmacokinetic Evaluation of Intravenous Hyaluronic Acid in Combination with Doxorubicin or 5-Fluorouracil," *Chemotherapy* 51:132-141.

Sakurai, K. et al. (1986). "Mucopolysaccharide-type Cancer-Metastasis Inhibitor," Japanese Kokai Patent Application No. Sho 61[1986]-17, with English translation, 36 pages.

Taguchi, T. et al. (Jan. 1994). "An Early Phase II Study of CPT-11 (irinotecan hydrochloride) in Patients with Advanced Breast Cancer," *Gan to Kagaku Ryoho* 21(1):83-90. (Abstract Only) one page.

Takasuna, K. et al. (Aug. 15, 1996). "Involvement of β-Glucuronidase in Intestinal Microflora in the Intestinal Toxicity of the Antitumor Camptothecin Derivative Irinotecan Hydrocholoride (CPT-11) in Rats," *Cancer Research* 56:3752-3757.

Turley, E.A. (Mar. 1992). "Hyaluronan and Cell Locomotion," *Cancer and Metastasis Reviews* 11:21-30.

Yamamoto, O.H. et al. (May 11, 1992). "Synthesis of the Conjugate of Adriamycin with Oxidized Hyaluronic Acid," *42nd Society of Polymer Science Japan Annual Conference Proceedings, Polymer Preprints*, Japan, May 31-Jun. 2, 1993, 42(3):898. (with English translation, eight pages.).

Yomota, C. (Jul. 3, 1997). "Research for Property Evaluation and Application of Hyaluronic Acid as a Biomedical Polymer," *1996 Human Science Fundamental Research Enterprise, Human Science Enterprise*, 16 pages (with English translation, 32 pages).

Anonymous. (Jul. 2008). "Sodium Hyaluronate," *European Pharmacopoeia* 62:3835-3837.

Final Office Action mailed Nov. 29, 2010, for U.S. Appl. No. 09/889,203, filed Mar. 13, 2002, 9 pages.

Gustafson, S. et al. (1995). "Studies on Receptors for Hyaluronan and the Turnover of Radioactively-Labelled Hyaluronan in Mice and Rats," *Second International Workshop on Hyaluronan in Drug Delivery, Round Table Series*, Willoughby, D.A. ed., Ontario, Canada, May 1-3, 1994, 36:5-7.

Hokputsa, S. et al. (2003). "Hydrodynamic Characterisation of Chemically Degraded Hyaluronic Acid," *Carbohydrate Polymers* 52:111-117.

Non-Final Office Action mailed, Nov. 15, 2010, for U.S. Appl. No. 11/191,407, filed Jul. 27, 2005, 11 pages.

Stern, R. et al. (2006). "Hyaluronan Fragments: An Information-Rich System," *European Journal of Cell Biology* 85:699-715.

Tsatas, D. et al. (2002). "EGF Receptor Modifies Cellular Responses to Hyaluronan in Glioblastoma Cells Lines," *Journal of Clinical Neuroscience* 9(3):282-288.

Brownlee, G.R. et al. (Apr. 2006). "Novel Formulations of Therapeutic Antibodies with Hyaluronic Acid (HA) in the Treatment of Colorectal Cancer: A Pre-clinical Evaluation," *Proceedings of the American Association for Cancer Research, 97th Annual Meeting*, Washington, DC, Apr. 1-5, 2006, 47:162, Abstract No. 682.

Pályi-Krekk, Z. et al. (Nov. 1, 2007). "Hyaluronan-Induced Masking of ErbB2 and CD44-Enhanced Trastuzumab Internalisation in Trastuzumab Resistant Breast Cancer," *European Journal of Cancer* 43(16):2423-2433.

Anonymous. (2003). "New Perspective of Anticancer Agents 1) Anti-HER2 Antibody, Anti-EGFR Antibody, Anti-VEGF Antibodies," *Surgery Frontier* 10(2):75-82. (English Translation and Translation Verification, pp. 1-10.).

Final Office Action mailed on Dec. 13, 2011, for U.S. Appl. No. 11/996,733, filed Jun. 19, 2008, thirty-four pages.

Rugo, H. (2004). "Bevacizumab in the Treatment of Breast Cancer: Rationale and Current Data," *The Oncologist* 9, suppl. 1, pp. 43-49.

Final Office Action mailed May 2, 2011, for U.S. Appl. No. 11/191,407, filed Jul. 27, 2005, 13 pages.

Mürdter, T.E. et al. (Jun. 15, 1997, e-published Jun. 1, 1997). "Enhanced Uptake of Doxorubicin into Bronchial Carcinoma: β-Glucuronidase Mediates Release of Doxorubicin froma Glucuronide Prodrug (HMR 1826) at the Tumor Site," *Cancer Research* 57:2440-2445.

Non-Final Office Action mailed Apr. 15, 2011, for U.S. Appl. No. 11/996,733, Internationally filed Jul. 27, 2006, 31 pages.

Non-Final Office Action mailed on Jun. 30, 2011, for U.S. Appl. No. 12/482,870, filed Jun. 11, 2009, eleven pages.

* cited by examiner

THERAPEUTIC COMPOSITIONS COMPRISING HYALURONAN AND THERAPEUTIC ANTIBODIES AS WELL AS METHODS OF TREATMENT

CROSS-REFERENCE TO RELATED APPLICATIONS

This application is a National Phase application under 35 U.S.C. §371 of International Application No. PCT/AU2006/001293 filed Sep. 4, 2006 and claims the benefit of U.S. Provisional Application Nos. 60/715,293 filed Sep. 7, 2005 and 60/788,589 filed Mar. 31, 2006, the disclosures of which are incorporated herein by reference in their entirety.

BACKGROUND OF THE INVENTION

1. Field of the Invention

The present invention relates generally to treatment and prophylactic protocols for cellular diseases or disorders, such as diseases and disorders associated with abnormal cellular proliferation. More particularly, the present invention provides compositions comprising therapeutic antibodies and hyaluronan and their use in the treatment or prophylaxis of cellular diseases and disorders.

2. Description of the Prior Art

All scientific citations, patents, patent applications and manufacturer's technical specifications referred to hereinafter are incorporated herein by reference in their entirety.

Cancer is a hyperproliferative cellular disease which occurs when a cell population replicates in the absence of normal genetic or biochemical control of the cell cycle. In the United States alone, 2,604,650 people died from cancer between 1990-1994, with more men (53%) than women (47%) affected. The most numerous cancer deaths were the result of cancer of the lung (~30%), colon and rectum (a 11%), breast (~8%), and prostate (~6.5%). Among women, the most commonly occurring cancers are breast (31%), lung (12%), colon and rectum (12%), uterus (6%) and ovary (4%).

Historically, cancer treatment generally requires a therapeutic protocol comprising one or more of surgery, radiation and chemotherapy. More recently, therapeutic antibodies directed to cancer targets have been developed. These antibodies are used as parenteral cytoxics and exhibit dose dependant efficacy and toxicity. Systemic chemotherapy is the main treatment available for localized or disseminated malignant disease. Chemotherapy, whether curative or palliative, requires multiple cycles of treatment where chemotherapeutic agents exhibit a dose-response effect and the cell kill correlates to the drug exposure.

The majority of therapeutic approaches to the development of tumor-selective treatments have focused on the morphological and functional differences between malignant and healthy tissues. Drugs designed to manipulate the morphological differences have relied upon the rapid proliferation of cancer cells which coincides with a requirement for an effective oxygen and nutrient supply often fulfilled by the process of neovascularization. The resultant tumor vasculature is defective which allows the penetration of large molecules into the extravascular space and due to the poor intra-tumoral lymphatic drainage there can be a preferential accumulation of large compounds within the malignant site.

The functional requirement for tumor cells to be metabolically efficient and motile results in an over-expression of numerous tumor-specific receptors which can be used as a selective target for the active delivery of anti-cancer agents via specific ligands against these epitopes. One mechanism of overcoming the poor specificity of current cancer therapies has been the use of antibodies which are directed to tumor-specific receptors or molecules. In addition, therapeutic antibodies have the potential to be effective agents in the treatment and prophylaxis of many diseases.

Humanized and deimmunized antibodies have great potential although generally are required to be delivered at a high dose and are expensive to produce. A prerequisite for effective antibody targeting is that antibodies should be able to penetrate tissues. In addition, it is preferable to have a local controlled release method that delivers antibodies to the site of disease. However, formulation challenges often result when coupling antibodies with delivery vehicles. Antibody penetration is a particular problem with tumor-associated therapeutic antibodies and research has also shown that the high affinity fragments can be retained in the periphery of tumors while medium and low affinity fragments appear to gain better penetration. In such cases, non-specific targeting of the antibody can become an issue.

As the development of monoclonal antibodies has moved away from mouse antibodies to chimeric, humanized and deimmunized antibodies, a reduction in anti-antibody response has been observed, however, potential concerns for repeated or chronic treatment exist in a clinical setting. Another possible side effect of antibody therapy is the cytokine release that is mediated through the recruitment of immune effector cells. There is a need, therefore, to develop antibody formulations which may improve efficacy or reduce side effects of antibodies or antibody fragments.

SUMMARY OF THE INVENTION

Throughout the specification, unless the context requires otherwise, the word "comprise", or variations such as "comprising" or "comprises", will be understood to imply the inclusion of the stated element or integer or group of elements or integers but not the exclusion of any other element or integer or group of elements or integers.

The present invention is predicated in part on the use of hyaluronan (HA) and its derivatives and synthesized and chemically modified forms and salts in combination with therapeutic antibodies or fragments, analogs, derivatives, portions, chimeras or deimmunized forms thereof to facilitate effective delivery of antibodies to the diseased site resulting in a minimally toxic but efficacious treatment regimen for proliferative cellular disease.

The present invention provides, therefore, antibody formulations and therapeutic and prophylactic protocols for cellular diseases and disorders.

Accordingly, one aspect of the present invention provides a formulation comprising HA or a derivative or synthesized or chemically modified form or salt thereof and a therapeutic antibody, or fragment, analog, derivative, portion, chimera or deimmunized form thereof and optionally one or more, pharmaceutically acceptable carriers, diluents and/or excipients.

Since HA is administered in high concentrations, there is a constant internalization of HA which means that any antibody which is in an equilibrium within the volumetric domain of the HA is co-internalized resulting in a concentrated intracellular release of the drug or pharmaceutical composition. In addition, the binding of HA to non-internalization receptors can facilitate the development of a HA/therapeutic antibody glycoclayx that can ensure a prolonged retention of the antibody at the cell surface resulting in an enhanced availability to the antibody epitope.

In accordance with the present invention, the combination of HA and an antibody facilitates improved efficacy of the antibody compared to use of the antibody in the absence of HA. "Improved efficacy" includes enhanced effectiveness at inhibiting the proliferation of cancer cells or rendering a cytotoxic effect upon cancer cells resulting in less tumor burden. The antibody formulations of the present invention are proposed to be useful in the treatment or prophylaxis of cellular diseases.

The present invention is predicated in part on the determination that HA and its derivatives, synthesized or chemically modified forms and salts thereof, not only inhibit cells per se, but also allow the safe administration of selected antibodies at standard, lower and higher doses to treat subjects including human and animals. In vivo administration of hyaluronan in combination with antibodies also enhances the therapeutic effect of these agents against cells that are refractory, thus preventing the subsequent emergence of multidrug resistance. Through the ability of HA to provide an alternative route of cellular internalization, i.e. via the lysosomal processing system, the combination of HA and therapeutic antibodies sensitize cells that would otherwise be resistant to the treatment through intrinsic or acquired resistance mechanisms.

Antibodies contemplated by the present invention include any antibodies which are specific for target cell types associated with, or having the potential to be associated with a cellular disease. Examples of such antibodies include: ABX-EGF; Alemtuzumab; Apolizumab; Bevacizumab; Cantuzumab; Cetuximab; cG250; cmc-544; Daclizumab; Epratuzumab; erlotinib; Gemtuzumab ozogamicin; hA20; HCBE-11; Hun901; Ibritumomab tiuxetan; IDEC 159; Infliximab; Lumiliximab; mAb 3F8; mAb b43.13; mAb BC8; mAb CC49-deltaCH2; mAb Ch14.18; mAb CP-675,206; mAb HeFi-1; mAb Hu3S193; mAb HuG1-M195; mAb huHMFG1; mAb J591; mAb MDX-CTLA4; mAb MiK-beta-1; MDX-010; MEDI-507; MLN2704; Pertuzumab; RAV12; Rituximab; SGN-30; SGN-40; Tositumomab; Trastuzumab (herceptin); TRM-1 (TRAIL R1 Mab); and Yttrium-ibritumomab.

A particular embodiment of the subject invention is directed to an antibody formulation comprising HA and cetuximab.

Another particular embodiment provides an antibody formulation comprising HA and bevacizumab.

Even yet another particular embodiment provides an antibody formulation comprising HA and herceptin.

Still another aspect provides a formulation comprising HA or a derivative or synthesized or chemically modified form thereof and an antibody selected from the list in Table 1.

These formulations optionally further comprise one or more pharmaceutically acceptable carriers, excipients and/or diluents.

A particular embodiment of the subject invention is directed to a formulation wherein the hyaluronan or analog or derivative or synthesized or modified form thereof is in the molecular weight range of about 360 Daltons to 20,000 kDaltons.

A particular embodiment of the subject invention is directed to a formulation wherein the hyaluronan or analog or derivative or synthesized or modified form thereof is in the molecular weight range of about 360 Daltons to 2000 kDaltons.

A particular embodiment of the subject invention is directed to a formulation wherein the hyaluronan or analog or derivative or synthesized or modified form thereof is in the molecular weight range of about 20 kDaltons to 1,500 kDaltons.

A particular embodiment of the subject invention is directed to a formulation wherein the hyaluronan or analog or derivative or synthesized or modified form thereof is in the modal molecular weight range of about 860 kDaltons.

A particular embodiment of the subject invention is directed to a formulation wherein the hyaluronan or analog or derivative or synthesized or modified form thereof and the antibody are not covalently bound.

A particular embodiment of the subject invention is directed to a formulation wherein the pH range of the composition is between pH 2.5 and 10.5.

A particular embodiment of the subject invention is directed to a formulation wherein the pH range of the composition is between pH 5.0 and 8.5.

A particular embodiment of the subject invention is directed to a formulation wherein the antibody, fragment, derivative, portion, chimera or fully de-immunized form thereof is for use in the treatment or prophylaxis of a cellular proliferative disease.

A particular embodiment of the subject invention is directed to a formulation wherein the antibody, fragment, derivative or portion thereof is selected from the group of antibodies consisting of: ABX-EGF; Alemtuzumab; Apolizumab; Bevacizumab; Cantuzumab; Cetuximab; cG250; cmc-544; Daclizumab; Epratuzumab; erlotinib; Gemtuzumab ozogamicin; hA20; HCBE-11; Hun901; Ibritumomab tiuxetan; IDEC 159; Infliximab; Lumiliximab; mAb 3F8; mAb b43.13; mAb BC8; mAb CC49-deltaCH2; mAb Ch14.18; mAb CP-675,206; mAb HeFi-1; mAb Hu3S193; mAb HuG1-M195; mAb huHMFG1; mAb J591; mAb MDX-CTLA4; mAb MiK-beta-1; MDX-010; MEDI-507; MLN2704; Pertuzumab; RAV12; Rituximab; SGN-30; SGN-40; Tositumomab; Trastuzumab (herceptin); TRM-1 (TRAIL R1 Mab); and Yttrium-ibritumomab.

A particular embodiment of the subject invention is directed to a formulation wherein the cellular proliferative disease is any one of cancer, neoplastic disease or any disease involving inflammation of tissue or release of inflammatory agents.

A particular embodiment of the subject invention is directed to a formulation wherein the cellular proliferative disease results in one or more of a tumor, neoplasm, uncontrolled hyper-proliferation or metastasis.

A particular embodiment of the subject invention is directed to a formulation wherein the cellular proliferative disease is present in one or more organs or tissues including the breast, lung, prostate, kidney, skin, neural tissue, ovary, uterus, liver, pancreas, epithelial cells, gastric tissue, intestine, exocrine, endocrine, lymphatic system, hematopoietic system, head tissue and neck tissue.

A particular embodiment of the subject invention is directed to a formulation wherein the cellular proliferative disease occurs in a mammal.

A particular embodiment of the subject invention is directed to a formulation wherein the antibody is cetuximab.

A particular embodiment of the subject invention is directed to a formulation wherein the antibody is bevacizumab.

A particular embodiment of the subject invention is directed to a formulation wherein the antibody is herceptin.

A particular embodiment of the subject invention is directed to a formulation wherein the antibody is humanized.

A particular embodiment of the subject invention is directed to a formulation for use in the treatment or prophylaxis of colorectal cancer.

A particular embodiment of the subject invention is directed to a formulation wherein the mammal is selected from the group consisting of primate, bovine, canine, equine, feline and porcine animal.

A particular embodiment of the subject invention is directed to a formulation wherein the primate is a human.

A particular embodiment of the subject invention is directed to a formulation wherein the composition is in oral, topical or parenteral form.

A particular embodiment of the subject invention is directed to a formulation wherein the oral form is presented as a tablet, pill, capsule, lozenge, troche, powder, granule, emulsion, liquid, aqueous or oily suspension, medicine, syrup, elixir or spray.

A particular embodiment of the subject invention is directed to a formulation wherein the topical form is administered in the form of a cream, lotion, emulsion, gel, film, spray, paste or ointment.

A particular embodiment of the subject invention is directed to a formulation wherein the parenteral form is administered by subcutaneous injection, aerosol, intravenous, intramuscular, intrathecal, intracranial, intrasternal injection or infusion techniques in the form of a liquid, ointment, suppository or pessary.

A particular embodiment of the subject invention is directed to a formulation together with a second agent or composition used in the treatment of cellular proliferative disease wherein the second agent is a chemotherapeutic agent or therapeutic antibody.

A particular embodiment of the subject invention is directed to a formulation wherein the second agent or composition is irinotecan or doxorubicin or fluorouracil or leucovorin or oxaliplatin or methotrexate or gemcitabine.

A particular embodiment of the subject invention is directed to a formulation wherein the bioavailability of the antibody, fragment, derivative or portion thereof is enhanced.

A particular embodiment of the subject invention is directed to a formulation wherein the HA is administered prior or subsequent to the administration of the agent.

A particular embodiment of the subject invention is directed to a formulation wherein the HA is administered prior to the administration of the agent.

A particular embodiment of the subject invention is directed to a formulation wherein the HA is administered subsequent to the administration of the agent.

A particular embodiment of the subject invention is directed to a formulation wherein the HA is orally administered.

A particular embodiment of the subject invention is directed to a formulation wherein the HA is administered in an amount of about 0.01 to about 40 mg/kg of body weight.

A particular embodiment of the subject invention is directed to a formulation wherein the HA is administered in an amount of about 0.1 to about 27 mg/kg of body weight.

A particular embodiment of the subject invention is directed to a formulation together with a second composition used in the treatment of cellular proliferative disease wherein the second composition comprises a chemotherapeutic agent or therapeutic antibody.

A particular embodiment of the subject invention is directed to a formulation together with a second composition used in the treatment of cellular proliferative disease wherein the second composition comprises HA or a derivative or synthesized or chemically modified form or salt thereof and chemotherapeutic agent or therapeutic antibody.

A particular embodiment of the subject invention is directed to a formulation comprising a cetuximab and HA or a derivative or synthesized or chemically modified form or salt thereof together with a second component, irinotecan.

In a related aspect, the present invention also provides methods of treatment or prophylaxis for cellular diseases in a subject, the method comprising administering to a subject in need thereof a therapeutic antibody or a fragment, derivative, portion, chimera or deimmunized form thereof and HA or an analog, a derivative or synthesized or chemically modified form or salt thereof for a time and under conditions for the symptoms of the cellular disease to be ameliorated.

In one embodiment, the present invention contemplates a method of treatment or prophylaxis of a subject with a cellular disease said method comprising administering to said subject an antibody formulation comprising HA and cetuximab.

Yet another embodiment of the instant invention relates to a method of treatment or prophylaxis of a cellular disease in a subject said method comprising administering to said subject an antibody formulation comprising HA and bevacizumab.

Still yet another embodiment of the instant invention relates to a method of treatment or prophylaxis of a cellular disease in a subject said method comprising administering to said subject an antibody formulation comprising HA and herceptin.

A particular embodiment of the subject invention is directed to a method of treatment or prophylaxis for cellular diseases in a subject, the method comprising administering to a subject in need thereof a therapeutic antibody or a fragment, analog, derivative, portion, chimera or fully de-immunized form thereof and HA or an analog, a derivative or synthesized or chemically modified form or salt thereof for a time and under conditions for the symptoms of the cellular disease to be ameliorated.

A particular embodiment of the subject invention is directed to a method wherein the hyaluronan or an analog or derivative or synthesized or modified form thereof is in the molecular weight range of 360 Dalton to 20,000 kDaltons.

A particular embodiment of the subject invention is directed to a method wherein the hyaluronan or an analog or derivative or synthesized or modified form thereof is in the molecular weight range of about 360 Daltons to 2000 kDaltons.

A particular embodiment of the subject invention is directed to a method wherein the hyaluronan or an analog or derivative or synthesized or modified form thereof is in the molecular weight range of about 20 kDaltons to 1,500 kDaltons.

A particular embodiment of the subject invention is directed to a method wherein the hyaluronan or an analog or derivative or synthesized or modified form thereof is in the modal molecular weight range of about 860 kDaltons.

A particular embodiment of the subject invention is directed to a method wherein the hyaluronan or an analog or derivative or synthesized or modified form thereof and the antibody are not covalently bound.

A particular embodiment of the subject invention is directed to a method wherein the pH range of the composition is between pH 2.5 and 10.5.

A particular embodiment of the subject invention is directed to a method wherein the antibody, fragment, derivative or portion thereof is selected from the group of antibodies consisting of: ABX-EGF; Alemtuzumab; Apolizumab; Bevacizumab; Cantuzumab; Cetuximab; cG250; cmc-544; Daclizumab; Epratuzumab; erlotinib; Gemtuzumab ozogamicin; hA20; HCBE-11; Hun901; Ibritumomab tiuxetan; IDEC 159; Infliximab; Lumiliximab; mAb 3F8; mAb b43.13; mAb BC8; mAb CC49-deltaCH2; mAb Ch14.18; mAb CP-675,206;

mAb HeFi-1; mAb Hu3S193; mAb HuG1-M195; mAb huH-MFG1; mAb J591; mAb MDX-CTLA4; mAb MiK-beta-1; MDX-010; MEDI-507; MLN2704; Pertuzumab; RAV12; Rituximab; SGN-30; SGN-40; Tositumomab; Trastuzumab (herceptin); TRM-1 (TRAIL R1 Mab); and Yttrium-ibritumomab.

A particular embodiment of the subject invention is directed to a method wherein the cellular proliferative disease is any one of cancer, neoplastic disease or any disease involving inflammation of tissue or release of inflammatory agents.

A particular embodiment of the subject invention is directed to a method wherein the cellular proliferative disease results in one or more of a tumor, neoplasm, uncontrolled hyper-proliferation or metastasis.

A particular embodiment of the subject invention is directed to a method wherein the cellular proliferative disease is present in one or more organs or tissues including the breast, lung, prostate, kidney, skin, neural tissue, ovary, uterus, liver, pancreas, epithelial cells, gastric tissue, intestine, exocrine, endocrine, lymphatic system, hematopoietic system, head tissue and neck tissue.

A particular embodiment of the subject invention is directed to a method wherein the cellular proliferative disease occurs in a mammal.

A particular embodiment of the subject invention is directed to a method wherein the antibody is cetuximab.

A particular embodiment of the subject invention is directed to a method wherein the antibody is bevacizumab.

A particular embodiment of the subject invention is directed to a method wherein the antibody is herceptin.

A particular embodiment of the subject invention is directed to a method for the treatment or prophylaxis of colorectal cancer.

A particular embodiment of the subject invention is directed to a method wherein the mammal is selected from the group consisting of primate, bovine, canine, equine, feline and porcine animal.

A particular embodiment of the subject invention is directed to a method wherein the primate is a human.

A particular embodiment of the subject invention is directed to a method wherein the treatment is administered orally, topically or parenterally.

A particular embodiment of the subject invention is directed to a method wherein the orally administered form is tablet, pill, capsule, lozenge, troche, powder, granule, emulsion, liquid, aqueous or oily suspension, medicine, syrup, elixir or spray.

A particular embodiment of the subject invention is directed to a method wherein the topically administered form is a cream, lotion, emulsion, gel, film, spray, paste or ointment.

A particular embodiment of the subject invention is directed to a method wherein the parental administration is by subcutaneous injection, aerosol, intravenous, intramuscular, intrathecal, intracranial, intrasternal injection or infusion techniques in the form of a liquid, ointment, suppository or pessary.

A particular embodiment of the subject invention is directed to a method wherein the hyaluronan or an analog or a derivative or synthesized or modified form thereof is administered simultaneously, sequentially, prior to, in combination, during or subsequent to the administration of the antibody, fragment, derivative or portion thereof.

A particular embodiment of the subject invention is directed to a method wherein a second composition comprises a chemotherapeutic agent or therapeutic antibody.

A particular embodiment of the subject invention is directed to a method wherein a second composition comprises HA or a derivative or synthesized or chemically modified form or salt thereof and chemotherapeutic agent or therapeutic antibody.

A particular embodiment of the subject invention is directed to a method wherein the second agent or composition comprises HA formulated with irinotecan or doxorubicin or fluorouracil or leucovorin or oxaliplatin or methotrexate or gemcitabine.

A particular embodiment of the subject invention is directed to a method wherein the second agent or composition comprises HA formulated with any of the antibodies listed in Table 1.

A particular embodiment of the subject invention is directed to a method wherein the second agent or composition comprises irinotecan or doxorubicin or fluorouracil or leucovorin or oxaliplatin or methotrexate or gemcitabine.

A particular embodiment of the subject invention is directed to a method wherein the second agent or composition comprises any of the antibodies in the group consisting of: ABX-EGF; Alemtuzumab; Apolizumab; Bevacizumab; Cantuzumab; Cetuximab; cG250; cmc-544; Daclizumab; Epratuzumab; erlotinib; Gemtuzumab ozogamicin; hA20; HCBE-11; Hun901; Ibritumomab tiuxetan; IDEC 159; Infliximab; Lumiliximab; mAb 3F8; mAb b43.13; mAb BC8; mAb CC49-deltaCH2; mAb Ch14.18; mAb CP-675,206; mAb HeFi-1; mAb Hu3S193; mAb HuG1-M195; mAb huH-MFG1; mAb J591; mAb MDX-CTLA4; mAb MiK-beta-1; MDX-010; MEDI-507; MLN2704; Pertuzumab; RAV12; Rituximab; SGN-30; SGN-40; Tositumomab; Trastuzumab (herceptin); TRM-1 (TRAIL R1 Mab); and Yttrium-ibritumomab.

A particular embodiment of the subject invention is directed to a method wherein the second agent or composition comprises the treatment regime FOLFOX (fluorouracil, leucovorin and oxaliplatin), FOLFIRI (comprising irinotecan, leucovorin and fluorouracil) and IFL (comprising irinotecan, fluorouracil and leucovorin).

A particular embodiment of the subject invention is directed to a method wherein the bioavailability of the antibody, fragment, derivative or portion thereof is enhanced.

Another aspect of the subject invention is directed to use of a therapeutic antibody or a fragment, derivative, portion, chimera or fully de-immunized form thereof, in combination with HA or its derivatives or synthesized or chemically modified forms or salts in the manufacture of a medicament for the treatment or prophylaxis of cellular disease.

In particular, the antibody formulations of the present invention may be used in the treatment or prophylaxis of colon cancer.

Additionally, the formulations of the present invention may further comprise one or more further therapeutic agents, such as an anti-cancer agent, an anti-viral agent, an anti-bacterial agent, an anti-fungal agent, or any other agent which further facilitates the treatment or prophylaxis of the cellular disease or disorder.

In a further embodiment, the antibody formulation of the present invention is administered as part of combination therapy.

Yet another particular embodiment of the present invention provides a formulation comprising hyaluronan and cetuximab administer in combination with a second formulation comprising hyaluronan and a second antibody or chemotherapeutic agent or treatment regime.

Even yet another particular embodiment of the present invention relates to a formulation comprising hyaluronan and bevacizumab administer in combination with a second formulation comprising hyaluronan and a second antibody or chemotherapeutic agent or treatment regime.

Still yet another particular embodiment of the present invention relates to a formulation comprising hyaluronan and herceptin administer in combination with a second formulation comprising hyaluronan and a second antibody or chemotherapeutic agent or treatment regime.

Again, the formulations may further comprise one or more pharmaceutically acceptable carriers, excipients and/or diluents.

The present invention further contemplates delivery systems for the subject formulations. In one embodiment, the HA and antibody are maintained separately and are admixed just prior to administration. In this embodiment, the HA and antibody may be administered through a single body tissue-invasive inlet device or through multiple body tissue-invasive inlet devices such as but not limited to syringes and needles. Consequently, simultaneous or sequential administration of the HA and antibody, in either order, is part of the present invention.

The present invention further provides for the use of a therapeutic antibody or a fragment, derivative, portion, chimera or deimmunized form thereof, in combination with HA or its derivatives or synthesized or chemically modified forms or salts in the manufacture of a medicament for the treatment or prophylaxis of cellular disease.

BRIEF DESCRIPTION OF THE FIGURES

FIG. 1A shows antitumor activity of HyERB (150/0.25) and ERB (0.25) monotherapy in nude mice bearing LIM1215 human colon xenografts.

FIG. 4A shows the treatments up to day 32 (the day of the last injection) after the commencement of treatment.

DETAILED DESCRIPTION OF THE INVENTION

Figure 1A:
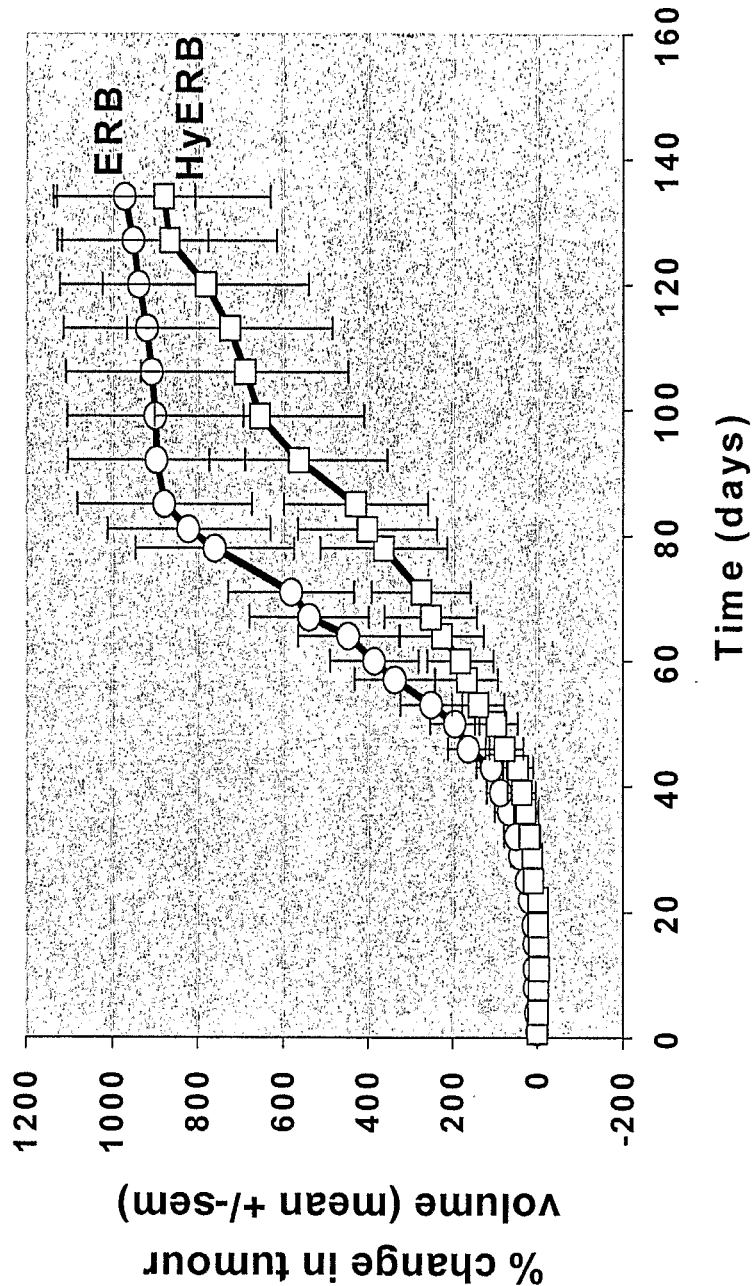
FIGS. 1A and B are a graphical representation illustrating the percentage change in tumor volume during the treatment of the mice bearing human colon cancer xenografts where the mice are treated with hyaluronan formulated with cetuximab (HyERB) or cetuximab (ERB) as a sole agent.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

All scientific citations, patents, patent applications and manufacturer's technical specifications referred to hereinafter are incorporated herein by reference in their entirety.

Reference to any prior art in this specification is not, and should not be taken as, an acknowledgment or any form of suggestion the prior art forms part of the common general knowledge in any country.

It is to be understood that unless otherwise indicated, the subject invention is not limited to specific formulation components, manufacturing methods, biological materials or reagents, dosage regimens and the like, as such may vary. It is also to be understood that the terminology used herein is for the purpose of describing particular embodiments only and is not intended to be limiting.

As used in the subject specification, the singular forms "a", "an" and "the" include plural aspects unless the context clearly dictates otherwise. Thus, for example, reference to "a formulation" includes a single formulation, as well as two or more formulations; reference to "an agent" or "a reagent" includes a single agent or reagent, as well as two or more agents or reagents; reference to "the cancer cell" includes a single cancer cell or group or tissue of cancer cells; and so forth.

The terms "compound", "agent", "reagent", "pharmacologically active agent", "medicament", "therapeutic", "active" and "drug" are used interchangeably herein to refer to an antibody or other interactive molecule which is to be or is formulated with HA or its chemically synthesized derivatives thereof and which are useful in the treatment or prophylaxis of cellular diseases and disorders. The terms also encompass pharmaceutically acceptable and pharmacologically active ingredients of those active agents specifically mentioned herein. When the terms "agent", "reagent", "compound", "pharmacologically active agent", "medicament", "therapeutic", "active" and "drug" are used, then it is to be understood that this includes the active entity per se as well as pharmaceutically acceptable, pharmacologically active salts, chimeras and recombinant forms of the antibodies or HA.

Reference to an "agent", "chemical agent", "compound", "pharmacologically active agent", "medicament", "therapeutic", "active" and "drug" includes combinations of two or more active agents. A "combination" also includes multi-part such as a two-part composition where the agents are provided separately and given or dispensed separately or admixed together prior to dispensation. For example, a multi-part pharmaceutical pack may have two or more agents separately maintained. Hence, this aspect of the present invention includes combination therapy. Combination therapy includes the co-administration of the antibody and HA or the antibody, HA and other.

The terms "effective amount" and "therapeutically effective amount" of an agent as used herein mean a sufficient amount of the agent to provide the desired therapeutic or physiological or effect or outcome. Such an effect or outcome includes reduction or amelioration of the symptoms of cellular disease. Undesirable effects, e.g. side effects, are sometimes manifested along with the desired therapeutic effect; hence, a practitioner balances the potential benefits against the potential risks in determining what an appropriate "effective amount" is. The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation. Generally, the agent or agents is/are given in an amount and under conditions sufficient to reduce inflammation and/or proliferation of cells.

The compositions and methods of the present invention are useful for increasing the sensitivity of cells to antibodies, such as those used in the treatment of cellular proliferative disease exemplified in Table 1. In particular the compositions and methods of the subject invention are useful for increasing the sensitivity of cells associated with cellular proliferative disorders, such as cancer. By increasing the efficacy without concomitant toxicity to non-cancer cells the present invention provides compositions and methods useful inter alia for treating cellular diseases such as cancer and preventing or reducing the chances of relapse and death as a result of cytotoxicity.

The term "subject" as used herein refers to any human or animal having a disease or condition which requires treatment with an antibody wherein the antibody has reduced efficacy relative to that desired. Generally, the subject is suffering from a cellular proliferative disorder, for example, cancer, neoplastic cell growth, etc. Reference to "cancer" includes a tumor or sarcoma as well as a hematological cancer such as leukemia. Subjects for the purposes of the present invention include, but are not limited to, mammals (e.g. primates, including humans, bovine, canine, equine, feline and porcine animals) and preferably humans.

By "cell proliferative disorder" is meant that a cell or cells demonstrate abnormal growth, typically aberrant growth which may lead to a neoplasm or a cancer.

Cell proliferative disorders include, for example, neoplastic diseases, cancers (eg., cancers of the breast, lung, prostate, kidney, skin, neural, ovary, uterus, liver, pancreas, epithelial, gastric, intestinal, exocrine, endocrine, lymphatic, haematopoietic system or head and neck tissue), fibrotic disorders and the like.

Generally, neoplastic diseases are conditions in which abnormal proliferation of cells results in a mass of tissue called a neoplasm or a cancer. Neoplasms have varying degrees of abnormalities in structure and behaviour. Some neoplasms are benign while others are malignant or cancerous. An effective treatment of neoplastic disease represents a valuable contribution to the search for cancer preventive or curative procedures.

The compounds and methods of the present invention are also proposed to be used to treat other diseases associated with antibody and chemotherapeutic treatment such as neurodegenerative disorders, hormonal imbalance and the like. Therefore, the present invention encompasses methods for ameliorating the symptoms of a disorder associated with cell proliferation, neoplasms, cancers and the like, including treating a subject having the disorder, at the site of the disorder, with HA and an antibody in an amount sufficient to inhibit or ameliorate the cell's proliferation or the disorder.

As used herein a "cancer" refers to a group of diseases and disorders that are characterized by uncontrolled cellular growth (e.g. formation of cell mass) without any differentiation of those cells into specialized and different cells. Cancers which can be treated using the methods of the present invention include, without being limited to, ABL1 protooncogene, AIDS related cancers, acoustic neuroma, acute lymphocytic leukaemia, acute myeloid leukaemia, adenocystic carcinoma, adrenocortical cancer, agnogenic myeloid metaplasia, alopecia, alveolar soft-part sarcoma, anal cancer, angiosarcoma, aplastic anaemia, astrocytoma, ataxia-telangiectasia, basal cell carcinoma (skin), bladder cancer, bone cancers, bowel cancer, brain stem glioma, brain and CNS tumors, breast cancer, CNS tumors, carcinoid tumors, cervical cancer, childhood brain tumors, childhood cancer, childhood leukaemia, childhood soft tissue sarcoma, chondrosarcoma, choriocarcinoma, chronic lymphocytic leukaemia, chronic myeloid leukaemia, colorectal cancers, cutaneous t-cell lymphoma, dermatofibrosarcoma-protuberans, desmoplastic-small-round-cell-tumor, ductal carcinoma, endocrine cancers, endometrial cancer, ependymoma, esophageal cancer, Ewing's sarcoma, extra-hepatic bile duct cancer, eye cancer, eye: melanoma, retinoblastoma, fallopian tube cancer, fanconi anaemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynaecological cancers, haematological malignancies, hairy cell leukaemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's-cell-histiocytosis, laryngeal cancer, leiomyosarcoma, leukaemia, li-fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid-tumor-of-kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, nijmegen breakage syndrome, non-melanoma skin cancer, non-small-cell-lung-cancer-(nsclc), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumors, pituitary cancer, polycythemia vera, prostate cancer, rare-cancers-and-associated-disorders, renal cell carcinoma, retinoblastoma, rhabdomyosarcoma, Rothmund-Thomson syndrome, salivary gland cancer, sarcoma, schwannoma, Sezary syndrome, skin cancer, small cell lung cancer (sclc), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/-ureter), trophoblastic cancer, urethral cancer, urinary system cancer, uroplakins, uterine sarcoma, uterus cancer, vaginal cancer, vulva cancer, Waldenstrom's-macroglobulinemia or Wilms' tumor. As indicated above, the term "cancer" covers tumors, sarcomas and leukemia's and all those terms may be used interchangeably.

The compounds of the present invention are utilized in pharmaceutical compositions by adding an effective amount of a compound to a suitable pharmaceutically acceptable excipient, diluent or carrier. Use of the compounds and methods of the present invention are also useful prophylactically.

The term "antibody" as used herein refers to an immunoglobulin molecule or immunologically active portion thereof, i.e., an antigen-binding portion and includes parts, domain antibodies, fragments, chimeras and deimmunized forms thereof. Examples of immunologically active portions of immunoglobulin molecules include scFV and dcFV fragments, F(ab) and F(ab')$^2$ fragments which are generated by treating the antibody with an enzyme such as papain or pepsin, respectively. The antibody can be a polyclonal, monoclonal, recombinant, e.g., a chimeric, humanized, deimmunized fully-human, non-human, e.g., murine, or single chain antibody. The antibody can be coupled to a toxin or imaging agent. Specifically, the antibodies of the instant invention are anti-cancer antibodies that have a therapeutic effect for a subject having a cell proliferative disorder, e.g., cancer. In specific embodiments, the antibodies are those listed in Table 1. In other embodiments, the antibodies bind a target listed in Table 1. In yet other embodiments, the antibodies are therapeutic antibodies that bind to a protein involved in the pathogenesis of cancer and have a beneficial effect for a subject. Chimeric, humanized, deimmunized but most preferably, completely human antibodies are desirable for therapeutic treatment of human patients.

TABLE 1

Examples of antibodies for use in cellular proliferative diseases especially cancer.

| Generic Name | Trade name (or alternate name) | Target |
|---|---|---|
| ABX-EGF | Panitumumab | EGFR |
| Alemtuzumab | Campath | CD52 |
| Apolizumab | Hu1D10 | 1D10 |
| Bevacizumab | Avastin | VEGF |
| Cantuzumab | | CanAg antigen |
| Cetuximab | Erbitux | EGFR |
| cG250 | Rencarex | MN antigen |
| cmc-544 | | CD22 |
| Daclizumab | Zenapax | CD25 |
| Epratuzumab | | CD22 |
| erlotinib | Tarceva | EGFR |
| Gemtuzumab ozogamicin | Mylotarg | CD33 |
| hA20 | | CD20 |
| HCBE-11 | | LTBR |
| Hun901 | BB-10901 | CD56 |
| Ibritumomab tiuxetan | Zevalin | CD20 |

TABLE 1-continued

Examples of antibodies for use in cellular proliferative diseases especially cancer.

| Generic Name | Trade name (or alternate name) | Target |
|---|---|---|
| IDEC 159 | | Tag72 |
| Infliximab | Remicade | TNF |
| Lumiliximab | | CD33 |
| mAb 3F8 | | Ganglioside GD2 |
| mAb b43.13 | | CA125 |
| mAb BC8 | | CD45 |
| mAb CC49-deltaCH2 | | TAG-72 |
| mAb Ch14.18 | | Ganglioside GD2 |
| mAb CP-675,206 | CP-675 | CTLA-4 |
| mAb HeFi-1 | | CD30 |
| mAb Hu3S193 | | Lewis-y antigen |
| mAb HuG1-M195 | | CD33 |
| mAb huHMFG1 | R1549 | Muc1 |
| mAb J591 | | Prostate specific membrane antigen |
| mAb MDX-CTLA4 | | CTLA4 |
| mAb MiK-beta-1 | | IL2 Receptor ☐ chain |
| MDX-010 | | CTLA4 |
| MEDI-507 | Siplizumab | CD2 |
| MLN2704 | | Prostate specific membrane antigen |
| Pertuzumab | rhuMab 2C4 | Her2 dimerization domain |
| RAV12 | | Glycoprotein RAAG12 |
| Rituximab | Rituxan | CD20 |
| SGN-30 | | CD30 |
| SGN-40 | | CD40 |
| Tositumomab | Bexxar | CD20 |
| Trastuzumab | Herceptin | Her2/neu |
| TRM-1 (TRAIL R1 Mab) | | TRAIL-1 receptor |
| Yttrium-ibritumomab | Zevalin | CD20 |

An antibody (or fragment thereof) may also be conjugated to a therapeutic moiety such as a cytotoxin, a therapeutic agent or a radioactive ion. A cytotoxin or cytotoxic agent includes any agent that is detrimental to cells. Examples include Taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine and 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin and anthramycin (AMC)), DM-1, and anti-mitotic agents (e.g., vincristine, vinblastine, taxol and maytansinoids). Radioactive ions include, but are not limited to iodine, yttrium and praseodymium.

The methods of the present invention involve in one embodiment, (1) the administration of HA, prior to, together with, or subsequent to the administration of an antibody; or (2) the administration of a combination of HA and an antibody.

As used herein, the term "therapeutically effective amount" is meant an amount of a compound of the present invention effective to yield a desired therapeutic response. For example, to prevent cancer or treat the symptoms of cancer in a host or an amount effective to treat cancer.

The specific "therapeutically effective amount" will vary with such factors as the particular condition being treated, the physical condition of the patient, the type of mammal being treated, the duration of the treatment, the nature of concurrent therapy (if any), and the specific formulations employed and the antibody.

As used herein, a "pharmaceutical carrier" is a pharmaceutically acceptable solvent, suspending agent or vehicle for delivering the HA and/or chemotherapeutic agent to the animal or human. The carrier may be liquid or solid and is selected with the planned manner of administration in mind.

As used herein, the term "cell" includes but is not limited to animal cells and particularly mammalian cells (e.g. human cells, mouse cells or rat cells).

The instant invention also provides compositions including one or more anti-cancer antibodies and derivatives, fragments and/or salts of HA. A number of derivatives and fragments of HA have been described in the literature and are intended to be included in the formulations and methods of the instant invention. HA may also be chemically modified or synthesized. HA may be referred to as a "polymer", "hyaluronic acid", "hyaluronate" or "hyaluronan".

Being a polymeric molecule, HA molecules may exhibit a range of varying molecule weights. HA formulations may, therefore, comprise molecules of different molecular weights. Almost any average of modal molecular weight formulation of HA may be effective in the methods of the present invention and the present invention is not limited to any particular size or size range of HA. HA having a modal molecular weight in the range 1 to 2 million daltons is considered particularly useful although the present invention is not so limited. Examples of useful molecular weights of HA include approximately in daltons 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990, 2000, 2010, 2020, 2030, 2040, 2050, 2060, 2070, 2080, 2090, 2100, 2110, 2120, 2130, 2140, 2150, 2160, 2170, 2180, 2190, 2200, 2210, 2220, 2230, 2240, 2250, 2260, 2270, 2280, 2290, 2300, 2310, 2320, 2330, 2340, 2350, 2360, 2370, 2380, 2390, 2400, 2410, 2420, 2430, 2440, 2450, 2460, 2470, 2480, 2490, 2500, 2510, 2520, 2530, 2540, 2550, 2560, 2570, 2580, 2590, 2600, 2610, 2620, 2630, 2640, 2650, 2660, 2670, 2680, 2690, 2700, 2710, 2720, 2730, 2740, 2750, 2760, 2770, 2780, 2790, 2800, 2810, 2820, 2830, 2840, 2850, 2860, 2870, 2880, 2890, 2900, 2910, 2920, 2930, 2940, 2950, 2960, 2970, 2980, 2990, 3000, 4000, 4010, 4020, 4030, 4040, 4050, 4060, 4070, 4080, 4090, 4100, 4110, 4120, 4130, 4140, 4150, 4160, 4170, 4180, 4190, 4200, 4210, 4220, 4230, 4240, 4250, 4260, 4270, 4280, 4290, 4300, 4310, 4320, 4330, 4340, 4350, 4360, 4370, 4380, 4390, 4400, 4410, 4420, 4430, 4440, 4450, 4460, 4470, 4480, 4490, 4500, 4510, 4520, 4530, 4540, 4550, 4560, 4570, 4580, 4590, 4600, 4610, 4620, 4630, 4640, 4650, 4660, 4670, 4680, 4690, 4700, 4710, 4720, 4730, 4740, 4750, 4760, 4770, 4780, 4790, 4800, 4810, 4820, 4830, 4840, 4850, 4860, 4870, 4880, 4890, 4900, 4910, 4920, 4930, 4940, 4950, 4960, 4970, 4980, 4990, 50005010, 5020, 5030, 5050, 5050, 5060, 5070, 5080, 5090, 5100, 5110, 5120, 5130, 5150, 5150, 5160, 5170, 5180, 5190, 5200, 5210, 5220, 5230, 5240, 5250, 5260, 5270, 5280, 5290, 5300, 5310, 5320, 5330, 5350, 5350, 5360, 5370, 5380, 5390, 5500, 5410, 5420, 5430, 5450, 5450, 5460, 5470, 5480, 5490, 5500, 5510, 5520, 5530, 5540, 5550, 5560, 5570, 5580, 5590, 5600, 5610, 5620, 5630, 5640, 5650, 5660, 5670, 5680, 5690, 5700, 5710, 5720, 5730, 5740, 5750, 5760, 5770, 5780, 5790, 5800, 5810, 5820, 5830, 5840, 5850, 5860, 5870, 5880, 5890, 5900, 5910, 5920, 5930, 5940, 5950, 5960, 5970, 5980, 5990, 6000, 6010, 6020, 6030, 6040, 6050, 6060, 6070, 6080, 6090, 6100, 6110, 6120, 6130, 6140, 6150, 6160, 6170, 6180, 6190, 6200, 6210, 6220, 6230, 6240, 6250, 6260, 6270, 6280, 6290, 6300, 6310, 6320, 6330, 6340, 6350, 6360, 6370, 6380, 6390, 6400, 6410, 6420, 6430, 6440, 6450, 6460, 6470, 6480, 6490, 6500, 4510, 6520, 4530, 6540, 6550, 6560, 6570, 6580, 6590, 6600, 6610, 6620, 6630, 6640, 6650, 6660, 6670, 6680, 6690, 6700, 6710, 6720, 6730, 6740, 6750, 6760, 6770, 6780, 6790, 6800, 6810, 6820, 6830, 6840, 6850, 6860, 6870, 6880, 6890, 6900, 6910, 6920, 6930, 6940, 6950, 6960, 6970, 6980, 6990, 7000, 7010, 7020, 7030, 7040, 7050, 7060, 7070, 7080, 7090, 7100, 7110, 7120, 7130, 7140, 7150, 7160, 7170, 7180, 7190, 7200, 7210, 7220, 7230, 7240, 7250, 7260, 7270, 7280, 7290, 7300, 7310, 7320, 7330, 7340, 7350, 7360, 7370, 7380, 7390, 7400, 7410, 7420, 7430, 7440, 7450, 7460, 7470, 7480, 7490, 7500, 7510, 7520, 7530, 7540, 7550, 7560, 7570, 7580, 7590, 7600, 7610, 7620, 7630, 7640, 7650, 7660, 7670, 7680, 7690, 7700, 7710, 7720, 7730, 7740, 7750, 7760, 7770, 7780, 7790, 7800, 7810, 7820, 7830, 7840, 7850, 7860, 7870, 7880, 7890, 7900, 7910, 7920, 7930, 7940, 7950, 7960, 7970, 7980, 7990, 8000, 8010, 8020, 8030, 8040, 8050, 8060, 8070, 8080, 8090, 8100, 8110, 8120, 8130, 8140, 8150, 8160, 8170, 8180, 8190, 8200, 8210, 8220, 8230, 8240, 8250, 8260, 8270, 8280, 8290, 8300, 8310, 8320, 8330, 8340, 8350, 8360, 8370, 8380, 8390, 8400, 8410, 8420, 8430, 8440, 8450, 8460, 8470, 8480, 8490, 8500, 8510, 8520, 8530, 8540, 8550, 8560, 8570, 8580, 8590, 8600, 8610, 8620, 8630, 8640, 8650, 8660, 8670, 8680, 8690, 8700, 8710, 8720, 8730, 8740, 8750, 8760, 8770, 8780, 8790, 8800, 8810, 8820, 8830, 8840, 8850, 8860, 8870, 8880, 8890, 8900, 8910, 8920, 8930, 8940, 8950, 8960, 8970, 8980, 8990, 9000, 9010, 9020, 9030, 9040, 9050, 9060, 9070, 9080, 9090, 9100, 9110, 9120, 9130, 9140, 9150, 9160, 9170, 9180, 9190, 9200, 9210, 9220, 9230, 9240, 9250, 9260, 9270, 9280, 9290, 9300, 9310, 9320, 9330, 9340, 9350, 9360, 9370, 9380, 9390, 9400, 9410, 9420, 9430, 9440, 9450, 9460, 9470, 9480, 9490, 9500, 9510, 9520, 9530, 9540, 9550, 9560, 9570, 9580, 9590, 9600, 9610, 9620, 9630, 9640, 9650, 9660, 9670, 9680, 9690, 9700, 9710, 9720, 9730, 9740, 9750, 9760, 9770, 9780, 9790, 9800, 9810, 9820, 9830, 9840, 9850, 9860, 9870, 9880, 9890, 9900, 9910, 9920, 9930, 9940, 9950, 9960, 9970, 9980, 9990, 10000, 10010, 10020, 10030, 10040, 10050, 10060, 10070, 10080, 10090, 10100, 10110, 10120, 10130, 10140, 10150, 10160, 10170, 10180, 10190, 10200, 10210, 10220, 10230, 10240, 10250, 10260, 10270, 10280, 10290, 10300, 10310, 10320, 10330, 10340, 10350, 10360, 10370, 10380, 10390, 10400, 10410, 10420, 10430, 104100, 10450, 10460, 10470, 10480, 10490, 10500, 10510, 10520, 10530, 10540, 10550, 10560, 10570, 10580, 10590, 10600, 10610, 10620, 10630, 10640, 10650, 10660, 10670, 10680, 10690, 10700, 10710, 10720, 10730, 10740, 10750, 10760, 10770, 10780, 10790, 10800, 10810, 10820, 10830, 10840, 10850, 10860, 10870, 10880, 10890, 10900, 10910, 10920, 10930, 10940, 10950, 10960, 10970, 10980, 10990, 11000, 11010, 11020, 11030, 11040, 11050, 11060, 11070, 11080, 11090, 11100, 11110, 11120, 11130, 11140, 11150, 11160, 11170, 11180, 11190, 11200, 11210, 11220, 11230, 11240, 11250, 11260, 11270, 11280, 11290, 11300, 11310, 11320, 11330, 11340, 11350, 11360, 11370, 11380, 11390, 11400, 11410, 11420, 11430, 114110, 11450, 11460, 11470, 11480, 11490, 11500, 11510, 11520, 11530, 11540, 11550, 11560, 11570, 11580, 11590, 11600, 11610, 11620, 11630, 11640, 11650, 11660, 11670, 11680, 11690, 11700, 11710, 11720, 11730, 11740, 11750, 11760, 11770, 11780, 11790, 11800, 11810, 11820, 11830, 11840, 11850, 11860, 11870, 11880, 11890, 11900, 11910, 11920, 11930, 11940, 11950, 11960, 11970, 11980, 11990, 12000, 12010, 12020, 12030, 12040, 12050, 12060, 12070, 12080, 12090, 12100, 12110, 12120, 12130, 12140, 12150, 12160, 12170, 12180, 12190, 12200, 12210, 12220, 12230, 12240, 12250, 12260, 12270, 12280, 12290, 12300, 12310, 12320, 12330, 12340, 12350, 12360, 12370, 12380, 12390, 12400, 12410, 12420, 12430, 124120, 12450, 12460, 12470, 12480, 12490, 12500, 12510, 12520, 12530, 12540, 12550, 12560, 12570, 12580, 12590, 12600, 12610, 12620, 12630, 12640, 12650, 12660, 12670, 12680, 12690, 12700, 12710, 12720, 12730, 12740, 12750, 12760, 12770, 12780, 12790, 12800, 12810, 12820, 12830, 12840, 12850, 12860, 12870, 12880, 12890, 12900, 12910, 12920, 12930, 12940, 12950, 12960, 12970, 12980, 12990, 13000, 13010, 13020, 13030, 13040, 13050, 13060, 13070, 13080, 13090, 13100, 13110, 13120, 13130, 13140, 13150, 13160, 13170, 13180, 13190, 13200, 13210, 13220, 13230, 13240, 13250, 13260, 13270, 13280, 13290, 13300, 13310, 13320, 13330, 13340, 13350, 13360, 13370, 13380, 13390, 13400, 13410, 13420, 13430, 134130, 13450, 13460, 13470, 13480, 13490, 13500, 13510, 13520, 13530, 13540, 13550, 13560, 13570, 13580, 13590, 13600, 13610, 13620, 13630, 13640, 13650, 13660, 13670, 13680, 13690, 13700, 13710, 13720, 13730, 13740, 13750, 13760, 13770, 13780, 13790, 13800, 13810, 13820, 13830, 13840, 13850, 13860, 13870, 13880, 13890, 13900, 13910, 13920, 13930, 13940, 13950, 13960, 13970, 13980, 13990, 14000, 14010, 14020, 14030, 14040, 14050, 14060, 14070, 14080, 14090, 14140, 14110, 14120, 14130, 14140, 14150, 14160, 14170, 14180, 14190, 14200, 14210, 14220, 14230, 14240, 14250, 14260, 14270, 14280, 14290, 14300, 14310, 14320, 14330, 14340, 14350, 14360, 14370, 14380, 14390, 14400, 14410, 14420, 14430, 144140, 14450, 14460, 14470, 14480, 14490, 14500, 14510, 14520, 14530, 14540, 14550, 14560, 14570, 14580, 14590, 14600, 14610, 14620, 14630, 14640, 14650, 14660, 14670, 14680, 14690, 14700, 14710, 14720, 14730, 14740, 14750, 14760, 14770, 14780, 14790, 14800, 14810, 14820, 14830, 14840, 14850, 14860, 14870, 14880, 14890, 14900, 14910, 14920, 14930, 14940, 14950, 14960, 14970, 14980, 14990, 15000, 15010, 15020, 15030, 15040, 15050, 15060, 15070, 15080, 15090, 15100, 15110, 15120, 15130, 15140, 15150, 15160, 15170, 15180, 15190, 15200, 15210, 15220, 15230, 15240, 15250, 15260, 15270, 15280, 15290, 15300, 15310, 15320, 15330, 15340, 15350, 15360, 15370, 15380, 15390, 15400, 15410, 15420, 15430, 154150, 15450, 15460, 15470, 15480, 15490, 15500, 15510, 15520, 15530, 15540, 15550, 15560, 15570, 15580, 15590, 15600, 15610, 15620, 15630, 15640, 15650, 15660, 15670, 15680, 15690, 15700, 10715, 15720, 15730, 15740, 15750, 15760, 15770, 15780, 15790, 15800, 15810, 15820, 15830, 15840, 15850, 15860, 15870, 15880, 15890, 15900, 15910, 15920, 15930, 15940, 15950, 15960, 15970, 15980, 15990, 16000, 16010, 16020, 16030, 16040, 16050, 16060, 16070, 16080, 16090, 16100, 16110, 16120, 16130, 16140, 16150, 16160, 16170, 16180, 16190, 16200, 16210, 16220, 16230, 16240, 16250, 16260, 16270, 16280, 16290, 16300, 16310, 16320, 16330, 16340, 16350, 16360, 16370, 16380, 16390, 16400, 16410, 16420, 16430, 164160, 16450, 16460, 16470, 16480, 16490, 16500, 16510, 16520, 16530, 16540, 16550, 16560, 16570, 16580, 16590, 16600, 16610, 16620, 16630, 16640, 16650, 16660, 16670, 16680, 16690, 16700, 16710, 16720, 16730, 16740, 16750, 16760, 16770, 16780, 16790, 16800, 16810, 16820, 16830, 16840, 16850, 16860, 16870, 16880, 16890, 16900, 16910, 16920, 16930, 16940, 16950, 16960, 16970, 16980, 16990, 17000, 17010, 17020, 17030, 17040, 17050, 17060, 17070, 17080, 17090, 17100, 17110, 17120, 17130, 17140, 17150, 17160, 17170, 17180, 17190, 17200, 17210, 17220, 17230, 17240, 17250, 17260, 17270, 17280, 17290, 17300, 17310, 17320, 17330, 17340, 17350, 17360, 17370, 17380, 17390, 17400, 17410, 17420, 17430, 174170, 17450, 17460, 17470, 17480, 17490, 17500, 17510, 17520, 17530, 17540, 17550, 17560, 17570, 17580, 17590, 17600, 17610, 17620, 17630, 17640, 17650, 17660, 17670, 17680, 17690, 17700, 17710, 17720, 17730, 17740, 17750, 17760, 17770, 17780, 17790, 17800, 17810, 17820, 17830, 17840, 17850, 17860, 17870, 17880, 17890, 17900, 17910, 17920, 17930, 17940, 17950, 17960, 17970, 17980, 17990, 18000, 18000, 18010, 18020, 18030, 18040, 18050, 18060, 18070, 18080, 18090, 18100, 18110, 18120, 18130, 18140, 18150, 18160, 18170, 18180, 18190, 18200, 18210, 18220, 18230, 18240, 18250, 18260, 18270, 18280, 18290, 18300, 18310, 18320, 18330, 18340, 18350, 18360, 18370, 18380, 18390, 18400, 18410, 18420, 18430, 184190, 18450, 18460, 18470, 18480, 18490, 18500, 18510, 18520, 18530, 18540, 18550, 18560, 18570, 18580, 18590, 18600, 18610, 18620, 18630, 18640, 18650, 18660, 18670, 18680, 18690, 18700, 18710, 18720, 18730, 18740, 18750, 18760, 18770, 18780, 18790, 18800, 18810, 18820, 18830, 18840, 18850, 18860, 18870, 18880, 18890, 18900, 18910, 18920, 18930, 18940, 18950, 18960, 18970, 18980, 18990, 19000, 19010, 19020, 19030, 19040, 19050, 19060, 19070, 19080, 19090, 19100, 19110, 19120, 19130, 19140, 19150, 19160, 19170, 19180, 19190, 19200, 19210, 19220, 19230, 19240, 19250, 19260, 19270, 19280, 19290, 19300, 19310, 19320, 19330, 19340, 19350, 19360, 19370, 19380, 19390, 19400, 19410, 19420, 19430, 194190, 19450, 19460, 19470, 19480, 19490, 19500, 19510, 19520, 19530, 19540, 19550, 19560, 19570, 19580, 19590, 19600, 19610, 19620, 19630, 19640, 19650, 19660, 19670, 19680, 19690, 19700, 19710, 19720, 19730, 19740, 19750, 19760, 19770, 19780, 19790, 19800, 19810, 19820, 19830, 19840, 19850, 19860, 19870, 19880, 19890, 19900, 19910, 19920, 19930, 19940, 19950, 19960, 19970, 19980, 19990, 20000, 20000, 20010, 20020, 20030, 20040, 20050, 20060, 20070, 20080, 20090, 20100, 20110, 20120, 20130, 20140, 20150, 20160, 20170, 20180, 20190, 20200, 20210, 20220, 20230, 20240, 20250, 20260, 20270, 20280, 20290, 20300, 20310, 20320, 20330, 20340, 20350, 20360, 20370, 20380, 20390, 20400, 20410, 20420, 20430, 204190, 20450, 20460, 20470, 20480, 20490, 20500, 20510, 20520, 20530, 20540, 20550, 20560, 20570, 20580, 20590, 20600, 20610, 20620, 20630, 20640, 20650, 20660, 20670, 20680, 20690, 20700, 20710, 20720, 20730, 20740, 20750, 20760, 20770, 20780, 20790, 20800, 20810, 20820, 20830, 20840, 20850, 20860, 20870, 20880, 20890, 20900, 20910, 20920, 20930, 20940, 20950, 20960, 20970, 20980, 20990, 21000, 21000, 21010, 21020, 21030, 21040, 21050, 21060, 21070, 21080, 21090, 21100, 21110, 21120, 21130, 21140, 21150, 21160, 21170, 21180, 21190, 21200, 21210, 21220, 21230, 21240, 21250, 21260, 21270, 21280, 21290, 21300, 21310, 21320, 21330, 21340, 21350, 21360, 21370, 21380, 21390, 21400, 21410, 21420, 21430, 214190, 21450, 21460, 21470, 21480, 21490, 21500, 21510, 21520, 21530, 21540, 21550, 21560, 21570, 21580, 21590, 21600, 21610, 21620, 21630, 21640, 21650, 21660, 21670, 21680, 21690, 21700, 21710, 21720, 21730, 21740, 21750, 21760, 21770, 21780, 21790, 21800, 21810, 21820, 21830, 21840, 21850, 21860, 21870, 21880, 21890, 21900, 21910, 21920, 21930, 21940, 21950, 21960, 21970, 21980, 21990, 22000, 22000, 22010, 22020, 22030, 22040, 22050, 22060, 22070, 22080, 22090, 22100, 22110, 22120, 22130, 22140, 22150, 22160, 22170, 22180, 22190, 22200, 22210, 22220, 22230, 22240, 22250, 22260, 22270, 22280, 22290, 22300, 22310, 22320, 22330, 22340, 22350, 22360, 22370, 22380, 22390, 22400, 22410, 22420, 22430, 224190, 22450, 22460, 22470, 22480, 22490, 22500, 22510, 22520, 22530, 22540, 22550, 22560, 22570, 22580, 22590, 22600, 22610, 22620, 22630, 22640, 22650, 22660, 22670, 22680, 22690, 22700, 22710, 22720, 22730, 22740, 22750, 22760, 22770, 22780, 22790, 22800, 22810, 22820, 22830, 22840, 22850, 22860, 22870, 22880, 22890, 22900, 22910, 22920, 22930, 22940, 22950, 22960, 22970, 22980, 22990, 23000, 23000, 23010, 23020, 23030, 23040, 23050, 23060, 23070, 23080, 23090, 23100, 23110, 23120, 23130, 23140, 23150, 23160, 23170, 23180, 23190, 23200, 23210, 23220, 23230, 23240, 23250, 23260, 23270, 23280, 23290, 23300, 23310, 23320, 23330, 23340, 23350, 23360, 23370, 23380, 23390, 23400, 23410, 23420, 23430, 234190, 23450, 23460, 23470, 23480, 23490, 23500, 23510, 23520, 23530, 23540, 23550, 23560, 23570, 23580, 23590, 23600, 23610, 23620, 23630, 23640, 23650, 23660, 23670, 23680, 23690, 23700, 23710, 23720, 23730, 23740, 23750, 23760, 23770, 23780, 23790, 23800, 23810, 23820, 23830, 23840, 23850, 23860, 23870, 23880, 23890, 23900, 23910, 23920, 23930, 23940, 23950, 23960, 23970, 23980, 23990, 24000, 24000, 24010, 24020, 24030, 24040, 24050, 24060, 24070, 24080, 24090, 24100, 24110, 24120, 24130, 24140, 24150, 24160, 24170, 24180, 24190, 24200, 24210, 24220, 24230, 24240, 24250, 24260, 24270, 24280, 24290, 24300, 24310, 24320, 24330, 24340, 24350, 24360, 24370, 24380, 24390, 24400, 24410, 24420, 24430, 244240, 24450, 24460, 24470, 24480, 24490, 24500, 24510, 24520, 24530, 24540, 24550, 24560, 24570, 24580, 24590, 24600, 24610, 24620, 24630, 24640, 24650, 24660, 24670, 24680, 24690, 24700, 24710, 24720, 24730, 24740, 24750, 24760, 24770, 24780, 24790, 24800, 24810, 24820, 24830, 24840, 24850, 24860, 24870, 24880, 24890, 24900, 24910, 24920, 24930, 24940, 24950, 24960, 24970, 24980, 24990, 25000, 30000, 35000, 40000, 45000, 50000, 55000, 60000, 65000, 70000, 75000, 80000, 85000, 90000, 95000, 100000, 200000, 300000, 400000, 500000, 600000, 700000, 800000, 900000, 1000000, 11000000, 12000000, 13000000, 14000000, 15000000, 16000000, 17000000, 18000000, 19000000, 20000000 daltons.

Exemplary HA derivatives are those described in U.S. Pat. No. 6,620,927 (thiol-modified hyaluronic acid derivatives); U.S. Pat. No. 6,552,184 (crosslinked compounds of hyaluronic acid and the derivatives thereof); U.S. Pat. No. 6,579,978 (sulphated compounds of hyaluronic acid and derivatives thereof); U.S. Pat. No. 6,831,172 (cross-linked hyaluronic acids and hemisuccinylated derivates thereof); U.S. Pat. No. 6,027,741 (sulfated hyaluronic acid and esters thereof); European Patent No. 0 138 572 (Hyaluronic acid fragments HYALECTIN and HYALASTINE); U.S. Pat. No. 4,851,521 (hyaluronic acid esters with different aromatic aliphatic and/or araliphatic alcohols); U.S. Pat. No. 5,202,431 (partial esters of hyaluronic acid); U.S. Pat. No. 5,676,964 (crosslinked hyaluronic acid polymers) and European Patent No. 0 265 116 (crosslinked esters of hyaluronic acid).

In addition to fragments and derivatives of hyaluronic acid, synthetic derivatives, i.e. semisynthetic derivatives may be used in the compositions and methods of the present invention. Exemplary semisynthetic derivatives of HA are esters of HA with alcohols of the aliphatic, araliphatic, heterocyclic and cycloaliphatic series, designated "HYAFF," that are described in U.S. Pat. Nos. 4,851,521, 4,965,353, and 5,202,431, European Patent No. 0 341 745 and European Patent No. 0 216 453. The contents of each of the above-identified patents are expressly incorporated herein by reference.

The HA and antibody compositions and methods of the present invention may be administered orally, topically, or parenterally in dosage unit formulations containing conventional non-toxic pharmaceutically acceptable carriers, excipients, adjuvants and vehicles.

The compositions and methods contemplated by the present invention include oral forms presented as a tablet, pill, capsule, lozenge, troche, powder, granule, emulsion, liquid, aqueous or oily suspension, medicine, syrup, elixir or spray.

The composition for oral use may contain one or more agents selected from the group of sweetening agents, flavoring agents, coloring agents and preserving agents in order to produce pharmaceutically elegant and palatable preparations. The tablets contain the active ingredient in admixture with non-toxic pharmaceutically acceptable excipients which are suitable for the manufacture of tablets.

These excipients may be, for example, (1) inert diluents, such as calcium carbonate, lactose, calcium phosphate or sodium phosphate; (2) granulating and disintegrating agents, such as corn starch or alginic acid; binding agents, such as starch, gelatin or acacia; and lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452 and 4,265,874 to form osmotic therapeutic tablets for control release.

In addition, the methods and compositions contemplated by the present invention include topical forms administered as a cream, lotion, emulsion, gel, film, spray, paste or ointment.

Furthermore, the compositions and methods contemplated by the present invention include parenteral administration and as used herein includes subcutaneous injections, aerosol, intravenous, intramuscular, intrathecal, intracranial and intrasternal injection, administration and infusion techniques. Parental formulations or compositions may be in the form of a liquid, ointment, suppository or pessary.

The HA as well as the antibodies useful in the method of the invention can be administered, for in vivo application, parenterally by injection or by gradual perfusion over time independently or together. Administration may be intravenously, intraperitoneally, intramuscularly, subcutaneously, intracavity, or transdermally. For in vitro studies the agents may be added or dissolved in an appropriate biologically acceptable buffer and added to a cell or tissue.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, anti-microbials, anti-oxidants, chelating agents, growth factors and inert gases and the like.

The compositions of the present invention may further comprising one or more chemotherapeutic agents or agents to reduce pain.

It is envisioned that the invention is used to treat pathologies associated cell proliferative disorders, including, for example, neoplasms, cancers (eg., cancers of the breast, lung, prostate, kidney, skin, neural, ovary, uterus, liver, pancreas, epithelial, gastric, intestinal, exocrine, endocrine, lymphatic, haematopoietic system or head and neck tissue), fibrotic disorders and the like.

The compounds and methods of the present invention may also be used to treat other diseases associated with cancer treatment such as neurodegenerative disorders, hormonal imbalance and the like. Therefore, the present invention encompasses methods for ameliorating a disorder associated with cell proliferation, neoplasms, cancers and the like, including treating a subject having the disorder, at the site of the disorder, with HA and an antibody in an amount sufficient to inhibit or ameliorate the cell's proliferation or the disorder.

Generally, the terms "treating", "treatment" and the like are used herein to mean affecting a subject, tissue or cell to obtain a desired pharmacologic and/or physiologic effect. The effect may be prophylactic in terms of completely or partially preventing a cell proliferative disorder or sign or symptom thereof, and/or may be therapeutic in terms of a partial or complete cure for a disorder and/or adverse effect attributable to, for example, aberrant cell proliferation. "Treating" as used herein covers any treatment of, or prevention of a cell proliferative disorder in a vertebrate, a mammal, particularly a human, and includes: (a) preventing the disorder from occurring in a subject that may be predisposed to the disorder, but has not yet been diagnosed as having it; (b) inhibiting the disorder, i.e., arresting its development; or (c) relieving or ameliorating the disorder, i.e., cause regression of the disorder. The present invention includes various pharmaceutical compositions useful for ameliorating cell proliferative disorder, including neoplasms, cancers and the like. The pharmaceutical compositions according to one embodiment of the subject invention are prepared by bringing HA, analogs, derivatives or synthesized or chemically modified forms thereof or salts thereof and one or more antibodies e.g., anticancer antibodies such as those identified in Table 1, or combinations of HA and one or more antibodies into a form suitable for administration to a subject using carriers, excipients and additives or auxiliaries. Also contemplated by the present inventions is a combination of HA with one or more antibodies together with one or more non-antibody-chemotherapeutic agent, such as, for example, paclitaxel, analgesics, opiates, hormones or antibiotics and the like. Additionally or alternatively, the formulation may comprise a pain relieving agent.

Frequently used "carriers" or "auxiliaries" include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in *Remington's Pharmaceutical Sciences*, 15th ed. Easton: Mack Publishing Co.: 1405-1412, 1461-1487, 1975 and *The National Formulary XIV.*, 14th ed. Washington: American Pharmaceutical Association, 1975 the contents of which are hereby incorporated by reference. The pH and exact concentration of the various components of the pharmaceutical composition are adjusted according to routine skills in the art. See Goodman and Gilman's *The Pharmacological Basis for Therapeutics* (7th ed.).

The pharmaceutical compositions are preferably prepared and administered in dose units. Solid dose units are tablets, capsules and suppositories. For treatment of a subject, depending on activity of the compound, manner of administration, nature and severity of the disorder, age and body weight of the subject, different daily doses can be used. Under certain circumstances, however, higher or lower daily doses may be appropriate. The administration of the daily dose can be carried out both by single administration in the form of an individual dose unit or else several smaller dose units and also by multiple administrations of subdivided doses at specific intervals.

The pharmaceutical compositions according to the invention may be administered locally or systemically in a therapeutically effective dose. Amounts effective for this use will depend on the severity of the disease and the weight and general state of the subject. Typically, dosages used in vitro may provide useful guidance in the amounts useful for in situ administration of the pharmaceutical composition, and animal models may be used to determine effective dosages for treatment of particular disorders. Various considerations are described, e.g. in Langer, *Science* 249 1527, 1990. Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such excipients may be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which may be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

HA together with an antibody of the present invention may also be administered in the form of liposome delivery systems, such as small unilamellar vesicles, large unilamellar vesicles and multilamellar vesicles. Liposomes can be formed from a variety of phospholipids, such as cholesterol, stearylamine, or phosphatidylcholines.

Dosage levels of the compounds of the present invention are of the order of about but not limited to 0.5 mg to about 10 mg per kilogram body weight, with a preferred dosage range between about 5 mg to about 20 mg per kilogram body weight per day (from about 0.3 g to about 1.2 g per patient per day). The amount of active ingredient that may be combined with the carrier materials to produce a single dosage will vary depending upon the host treated and the particular mode of administration. For example, a formulation intended for oral administration to humans may contain about 5 mg to 1 g of an active compound with an appropriate and convenient amount of carrier material which may vary from about 5 to 95 percent of the total composition. Dosage unit forms will generally contain between from about 5 mg to 500 mg of combined active ingredient or individual active ingredient.

It will be understood, however, that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy.

In addition, some of the compounds of the instant invention may form solvates with water or common organic solvents. Such solvates are encompassed within the scope of the invention.

The formulations of the present invention may be administered as a monotherapy (see examples in Table 2) or combination therapy to provide an operative treatment. It is intended to include any chemically compatible combination of chemotherapeutic agents, including antibodies and non-antibody therapeutics. Table 3 below provides a non-limiting list of examples of the types of combination therapies contemplated by the present invention.

TABLE 2

Monotherapy formulations
Formulation

HA and ABX-EGF
HA and Alemtuzumab
HA and Apolizumab
HA and Bevacizumab
HA and Cantuzumab
HA and Cetuximab
HA and cG250
HA and cmc-544
HA and Daclizumab
HA and Epratuzumab
HA and erlotinib
HA and Gemtuzumab ozogamicin
HA and hA20
HA and HCBE-11
HA and Hun901
HA and Ibritumomab tiuxetan
HA and IDEC 159
HA and Infliximab
HA and Lumiliximab
HA and mAb 3F8
HA and mAb b43.13
HA and mAb BC8
HA and mAb CC49-deltaCH2
HA and mAb Ch14.18
HA and mAb CP-675,206
HA and mAb HeFi-1

TABLE 2-continued

Monotherapy formulations
Formulation

HA and mAb Hu3S193
HA and mAb HuG1-M195
HA and mAb huHMFG1
HA and mAb J591
HA and mAb MDX-CTLA4
HA and mAb MiK-beta-1
HA and MDX-010
HA and MEDI-507
HA and MLN2704
HA and Pertuzumab
HA and RAV12
HA and Rituximab
HA and SGN-30
HA and SGN-40
HA and Tositumomab
HA and Trastuzumab
HA and TRM-1 (TRAIL R1 Mab)
HA and Yttrium-ibritumomab

TABLE 3

Examples of Combination Therapies

| First component* | Second or further components/treatments |
| --- | --- |
| HA and antibody | HA and antibody* |
| HA and antibody | HA and chemotherapeutic agent (for example, but not limited to, irinotecan or doxorubicin or fluorouracil or leucovorin or oxaliplatin or methotrexate or gemcitabine) |
| HA and antibody | Chemotherapeutic agent alone (for example, but not limited to, irinotecan or doxorubicin or fluorouracil or leucovorin or oxaliplatin or methotrexate or gemcitabine) |
| HA and antibody | Chemotherapy treatment regimes (for example, but not limited to, FOLFOX, FOLFIRI, IFL) |
| HA and antibody | antibody |
| HA and antibody | Radiation treatment |
| HA and antibody | Surgery |
| Antibody | HA and antibody (for examples see Table 1) |
| Antibody | HA and Chemotherapeutic agent (for example, but not limited to, irinotecan or doxorubicin or fluorouracil or leucovorin or oxaliplatin or methotrexate or gemcitabine) |
| Antibody | HA and chemotherapy treatment regimes (for example, but not limited to, FOLFOX, FOLFIRI, IFL) |

*see Table 2, above for examples which include HA and cetuximab (HyERB), HA and bevacizumab (HyBEV), etc The antibody formulation of the present invention may be used in a combination with various standard chemotherapy treatments. Such standard treatments include, for example, FOLFOX (fluorouracil, leucovorin and oxaliplatin), FOLFIRI (comprising irinotecan, leucovorin and fluorouracil) and IFL (comprising irinotecan, fluorouracil and leucovorin). These standard treatments are well known to a person of ordinary skill in the art.

The subject invention is now further described by way of reference only to the following non-limiting examples. It should be understood, however, that the examples following are illustrative only, and should not be taken in any way as a restriction on the generality of the invention described above. In particular, while the present invention is described in detail in relation to cancer, it will be clearly understood that the findings herein are not limited to treatment of cancer. For example, HA/antibody compositions may be used for treatment of other conditions such as infection by pathogenic agents.

The following Examples can be performed to test the efficacy of antibodies administered subsequent to, or in combination with HA for the treatment of cell proliferative disorders. The cell lines used in these experiments are obtainable from, for example, the American Type Culture Collection (ATCC) located in Manassas, Va., USA.

The Examples described below are only one set of experiments that can be performed.

One skilled in the art will understand that any given antibody can be tested on a number of different types of cancer, and that the specific type of cancer cells used in the examples are only one of the multiple cell types that can be used.

The following non-limiting examples are illustrative of the invention. All documents mentioned herein are incorporated herein by reference in their entirety.

EXAMPLE 1

Effect of HA and Anticancer Antibodies on Cancer Cells In Vitro

The following example sets forth how one of skill in the art can compare the effects of any one of the antibodies listed in Table 1 when formulated with HA for the treatment of a hyperproliferative disease such as cancer.

A cancer cell line is grown and subcultured as a monolayer in 175 cm$^2$ culture flasks in Leibovitz L-15 Medium supplemented with 10% v/v Fetal calf serum (FCS) and antibiotic/antimycotic reagents at 37° C. in humidity controlled incubator with 100% v/v air.

For the tests, cell lines are grown in 90% Leibovitz L-15 medium supplemented with 10% v/v FCS. When confluent the cultures are washed 1× in HBSS and trypsinized in 0.25% w/v trypsin/0.05% w/v EDTA. The cell suspension is counted with an automated cell counter (ZM-2 Coulter Counter) by adding 15 mL saline+0.2 ml of cell suspension. Cells are resuspended to a number of between 5,000 and 50,000 cells/ml of media.

The cells are plated into 48-well plates (1 cm$^2$ surface area) by adding 1 ml of cell suspension per well.

Cells are allowed to attach for 24 hours, before the media is removed, monolayers washed. The test media contains growth media containing anticancer antibodies formulated with hyaluronan as a sole therapy or in combination with standard chemotherapeutic agents.

The cells are exposed to the several formulations of HA/antibodies as a sole therapy or in combination with standard chemotherapeutic agents for different times and at different concentrations.

After the incubation and growth periods the cell monolayers are washed with HBSS and trypsinized. The cell suspension is counted with an automated cell counter by adding saline+cell suspension. Results are expressed as % of no drug control which is calculated as:

$$\frac{\text{Cell count} \times 100}{\text{Cells in no drug control}}$$

Or depending on the experiment as % of drug control, calculated as:

$$\frac{\text{Cell count} \times 100}{\text{Cells in drug control}}$$

The increase in treatment efficacy is determined by comparing the concentration of the HA antibody and/or chemotherapeutic agent combination required to render a cytotoxic effect on 50% of the cell population (IC$_{50}$).

EXAMPLE 2

Efficacy of Anticancer Antibodies Formulated with Hyaluronan In Vivo

Based on the results from the in vitro drug sensitivity experiments in Example 1, evaluation of the treatment efficacy of hyaluronan formulated with anticancer antibodies for the treatment cancer in vivo will be evaluated.

Cell lines are grown and subcultured as previously described in Example 1. For injection into mice, cells are grown to 80% confluency, trypsinized, washed twice by centrifugation, counted and resuspended in serum-free Leibovitz L-15 medium.

Six to eight weeks old athymic CBA/WEHI nude mice are maintained under specific pathogen-free conditions, with sterilized food and water available ad libitum. Each mouse receives one injection containing approximately 5×10$^6$ cells in 50 µl. Tumor measurements are made weekly by measuring three perpendicular diameters ($d_1 d_2 d_3$). Tumor volume is estimated using the formula:

$$(\tfrac{1}{6})\pi(d_1 d_2 d_3)$$

Treatment with anticancer antibodies and HA are commenced when tumor volume reaches 50-100 mm$^3$. Individual injections of anticancer antibodies formulated with HA are prepared according to individual mouse masses, with the aim of delivering a therapeutically effective does to each mouse.

Animals are weighed and tumor volumes are measured on the day of treatment application. Animals are injected via the tail vein.

The experimental end-point occurs when:
1. Tumor mass is so large the animal is immobilized;
2. Animal is not eating or drinking and has experienced dramatic weight loss; or
3. Tumor size is greater than 10% of body mass.

At the experimental end-point the animals are anaesthetized by intra-peritoneal injection of Nembutal, blood is collected followed by killing of the animals using cervical dislocation.

Immediately after killing the mouse the tumor, liver, heart, spleen, bladder, left and right kidneys, uterus, lungs, stomach, intestines, brain and lymph nodes are excized and placed in formalin and cetylpyridinium chloride. The tissue is fixed for 16-24 h before histological processing. Fixed tissue is dehydrated stepwise to 100% ethanol and embedded in paraffin blocks from which sections are placed on glass microscope slides. Staining the tissue sections with a haematoxylin nuclear stain and eosin cytoplasmic stain highlights any pathological features that could indicate treatment toxicity.

Lymph nodes which drained the tumor area are collected from each animal.

The haematoxylin and eosin stained lymph nodes are examined where each node will be microscopically examined for the presence of tumor cells. The CEA immunostained lymph nodes are microscopically examined, where any positively stained nodes are counted and considered positive for lymph node metastasis.

Tumor volume is monitored on a daily or weekly basis by caliper measurements and tumor volume calculated as previously described.

For demonstration of any weight changes the animal body weight is normalized to the body weight at the time of treatment commencement as Body mass (ex tumor)−body mass at commencement of treatment (ex tumor)

Body mass at commencement of treatment (ex tumor)×100

Effect of Treatment on Organ Mass

To ensure that treatment does not induce organ atrophy or enlargement, the organs are removed and weighed during the post mortem. The mass of each organ will be calculated as a % of the overall net body weight, and compared to the organ masses of a control group.

The overall animal survival time is calculated as the time (days or weeks) that the animal lived after the commencement of treatment.

EXAMPLE 3

Evaluation of the Effect of Hyaluronan on the Anti-Tumoral Properties of Cetuximab (Erbitux) in the Treatment of Human Colon Cancer To evaluate the effect of hyaluronan on the efficacy of therapeutic doses of cetuximab in the treatment of both colon cancer in nude mice as either monotherapy or in combination with irinotecan or its hyaluronan formulation (HyCAMP). Specific consideration of the follow efficacy parameters:
Primary Tumor Volume
Cancer Metastasis
Treatment toxicity in relation to
  Body mass
  Organ mass
  Survival
Test and Control Articles The test articles and dosages which will be used in the study are as follows:
Hyaluronic Acid (800-900 kD modal molecular weight); dosage 150 mg/kg or 26.6 mg/kg
Cetuximab (Erbitux; or ERB); dosage 0.5 mg/kg
Irinotecan Hydrochloride (Camptosar or CPT-11); dosage 50 mg/kg
HyERB (150/0.25) containing 150 mg/kg HA & 0.25 mg/kg cetuximab
HyERB (150/0.5) containing 150 mg/kg HA & 0.5 mg/kg cetuximab
HyCAMP (26.6/50) containing 26.6 mg/kg HA & 50 mg/kg irinotecan Human Colon Carcinoma Cell Line The human colon carcinoma cell line LIM1215 colon carcinoma cell line was routinely cultured as monolayer in 75 cm$^2$ culture flasks in RPMI1640 media supplemented with 5% v/v fetal calf serum, 10 μg/ml bovine insulin, 1 mM hydrocortisone and antibacterial/antimycotic stock. For generation of the primary tumor and injection into mice, cells were grown to 80% confluency, trypsinized in 0.05% trypsin/0.01% w/v EDTA solution, washed twice by centrifugation in a Beckman TJ-6 bench centrifuge at 400 gav for 10 min, and counted using a Coulter counter then resuspended in RPMI 1640 media at $2 \times 10^8$ cell/ml. This cell line was chosen due to its CD44 receptor, its responsiveness to irinotecan only or when formulated with HA (HyCAMP) compared with irinotecan chemotherapy in a xenograft model and that cellular proliferation is controlled by TGF-a/EGF-R autocrine loop.

Mouse Tumor Model

Athymic CBA/WEHI nude female mice, were maintained under specific pathogen-free conditions, with sterilized food and water available ad libitum. Each mouse received one injection containing $1 \times 10^7$ cells in 50-100 μl. The cells were injected with a 26-gauge needle into the mammary fat pad directly under the first nipple.

Treatment with (i) saline, (ii) HA, (iii) cetuximab (ERB), (iv) the formulation comprising HA & cetuximab (HyERB), (v) cetuximab/irinotecan and (vi) HA & cetuximab/HA & irinotecan (HyERB/HyCAMP) was commenced approximately 4-8 weeks after the tumor volume was in the range of 50-100 mm$^2$. Therapies were delivered by bolus IV on day 1 and 4 for a total of 5-weeks. Administration of irinotecan or HyCAMP was day 1 of a 7-day cycle for a total of 5-weeks. Mice were observed for 120-days for tumor re-growth. Table 4 below provides the dosage components and the mean tumor volume of each treatment group at commencement of treatment.

TABLE 4

Tumor volume at commencement of treatment

| Treatment Group* | Dosage of components in first formulation per animal (mg/kg) | | Dosage of components in second formulation per animal (mg/kg) | | Tumor volume at commencement of treatment Mean ± SD | |
| --- | --- | --- | --- | --- | --- | --- |
| | HA | cetuximab | HA | irinotecan | Tumor volume (mm$^3$) | as % of body mass |
| Control: Saline | — | — | — | — | 79.54 ± 8.2 | 0.46 ± 0.07 |
| Control: HA-only | 150 | — | — | — | 81.13 ± 11.7 | 0.46 ± 0.07 |
| Monotherapy: HA & cetuximab = HyERB(150/0.5) | 150 | 0.5 | — | — | 53.51 ± 3.8 | 0.27 ± 0.03 |
| Monotherapy: HA & cetuximab = HyERB(150/0.25) | 150 | 0.25 | — | — | 53.51 ± 3.8 | 0.27 ± 0.03 |
| Monotherapy: Cetuximab-only ERB(0.5) | — | 0.5 | — | — | 56.27 ± 6.9 | 0.28 ± 0.06 |
| Monotherapy: Cetuximab-only ERB(0.25) | — | 0.25 | — | — | 56.27 ± 6.9 | 0.28 ± 0.06 |
| Combination therapy: HA & cetuximab (HyERB) with HA & irinotecan (HyCAMP) = HyERB/HyCAMP | 150 | 0.5 | 26.6 | 50 | 76.1 ± 6.9 | 0.52 ± 0.08 |

TABLE 4-continued

| | Tumor volume at commencement of treatment | | | | | |
|---|---|---|---|---|---|---|
| | Dosage of components in first formulation per animal (mg/kg) | | Dosage of components in second formulation per animal (mg/kg) | | Tumor volume at commencement of treatment Mean ± SD | |
| Treatment Group* | HA | cetuximab | HA | irinotecan | Tumor volume (mm$^3$) | as % of body mass |
| Combination therapy: cetuximab & irinotecan = ERB/CAMP or ERB/CPT-11 | — | 0.5 | — | 50 | 71.63 ± 5.96 | 0.51 ± 0.06 |

*8 animals per treatment group.

Animal Maintenance and Housing

Athymic CBA/WEHI nude female mice, 6 to 8 weeks old, were maintained under specific pathogen-free conditions, with sterilized food and water available ad libitum. It has been experimentally proven that stress can be a major factor in a patient's response to chemotherapy therefore it will be ensured that equal numbers of mice are allocated to each cage.

Administration of Drugs and Control Vehicles

The mice were randomly distributed into each of six treatment groups (n=8 per group). Individual mice were placed in an injection box and treatment administration was via the tail vein using a 26-gauge needle. To ensure the accuracy of each administered dosage, syringes were weighed before and after injection using an analytical; four decimal place balance.

The administration schedule for each group is listed in Table 5 below.

parable antitumor activity. These dosages are therefore chosen as a reference point for treatment in this study where mice received a dose of 0.35 mg/injection.

A sterile stock solution of 20 mg/ml of irinotecan and diluted to 4 mg/mL in 0.9% (w/v) pyrogen-free injection grade NaCl and used to prepare injections of irinotecan formulated with HA.

Individual injections were prepared according to individual mouse masses, with the aim of delivering 50 mg/kg irintoecan (equivalent to human therapeutic dose of 208 mg/m$^2$; MIMS 1999). Single batches of 10 mg/mL solution were prepared and packaged into single use 100 mL sterile glass vials and undergo standard chemical and microbiology testing. Hyaluronan formulated with irinotecan [HyCAMP (150/50)] was prepared by mixing a portion of the 4 mg/ml irinotecan stock with the hyaluronan solution to a final HA concentration equivalent to 150 mg/kg of mouse mass and 50

TABLE 5

| | Treatment administration protocol | | | | |
|---|---|---|---|---|---|
| | Dosage of components in first formulation per animal (mg/kg) | | Dosage of components in second formulation per animal (mg/kg) | | Administration |
| Treatment Group* | HA | cetuximab | HA | irinotecan | Protocol |
| Control: Saline | — | — | — | — | Day 1, 4 × 5 weeks |
| Control: HA-only | 150 | — | — | — | Day 1, 4 × 5 weeks |
| Monotherapy: HyERB(150/0.5) | 150 | 0.5 | — | — | Day 1, 4 × 5 weeks |
| Monotherapy: HyERB(150/0.25) | 150 | 0.25 | — | — | Day 1, 4 × 5 weeks |
| Monotherapy: ERB(0.5) | — | 0.5 | — | — | Day 1, 4 × 5 weeks |
| Monotherapy: ERB (0.25) | — | 0.25 | — | — | Day 1, 4 × 5 weeks |
| Combination therapy: HA & cetuximab (HyERB) with HA & irinotecan (HyCAMP) = HyERB/HyCAMP | 150 | 0.5 | 26.6 | 50 | Day 1, 4 × 5 weeks Day 1, 8 × 5 weeks |
| Combination therapy: cetuximab & irinotecan = ERB/CAMP or ERB/CPT-11 | — | 0.5 | — | 50 | Day 1, 4 × 5 weeks Day 1, 8 × 5 weeks |

A sterile stock of cetuximab (Erbitux) was purchased as a single vial containing 100 mg in a final volume of 50 mL (2 mg/mL). Pre-clinical data in the GEO xenograft model demonstrates that a dosaging regimen of 0.25 to 1 mg/injection given every 3 days for a total of 5-doses is considered optimal in the delay of tumor growth. Alternate regimens of 0.25 mg/injection given twice weekly (days 1 and 4) for 5 weeks in the same xenograft model as well as 0.25-, 0.5 and 1 mg/injection twice weekly (days 1 and 4) for 3 weeks show commg/kg irinotecan. Hyaluronan formulated with cetuximab [HyERB(150/0.5)] was prepared by mixing a portion of 2 mg/mL cetuximab stock with the HA solution to a final HA concentration of 150 mg/kg of mouse mass and 0.5 mg/kg cetuximab.

The treatments were quantitatively administered via the tail vein. The injection syringe was weighed before and after injection and the weights recorded. The dose administered was calculated using the following formulas:

volume injected (ml) = mass of syringe before injection (g) − mass of syringe after injection (g)

concentration in injection solution in (mg/ml) = stock solution concentration × dilution factor Mass injected (mg) = concentration in injection solution (mg/ml) × volume injected (ml)

$$\text{Dose administered (mg/kg)} = \frac{\text{mass injected (mg)} \times 1000}{\text{mouse mass (g)}}$$

Monitoring of Body Mass, Tumor Volume and Animal Well Being

Upon commencement of treatment, animal observations were made on a daily basis, including the day of experimental end-point and recorded. Animals were weighed, tumor volumes measured and animal well being monitored by noting energy levels and evidence of GI tract toxicity such as diarrhoea. Weight loss was monitored by calculating net body weight as estimated by subtracting tumor weight, which is calculated as 1 g×tumor volume (cm³). For demonstration of any weight changes the animal body weight was normalized to the body weight at the time of treatment commencement as:

$$\frac{\text{Body mass (ex tumor)} - \text{Body mass at commencement of treatment (ex tumor)} \times 100}{\text{Body mass at commencement of treatment (ex tumor)}}$$

Killing of Animals at Experimental End-Point

At the experimental end-point the animals were anaesthetized by a 0.1 ml intra-peritoneal injection of Nembutal (60 mg/ml), blood was collected followed by killing of the animals using cervical dislocation.

Collection and Processing of Tumor and Body Organs

Immediately after killing the mouse the tumor, liver, heart, spleen, bladder, left and right kidneys, uterus, lungs, stomach, intestines, brain and lymph nodes were excized and weighed and placed in 10% formalin buffer. The tissues were fixed for 16-24 h before histological processing. Fixed tissue were dehydrated stepwise to 100% ethanol and embedded in paraffin blocks from which 2-4 μm sections were placed on glass microscope slides. The tissue sections were stained with a haematoxylin nuclear stain and eosin cytoplasmic stain. The organ sections were examined for features that could indicate treatment toxicity and for the presence of tumor cells.

Analysis of Data

Comparison of treatment and control group data were achieved by statistical analysis using parametric t-test analysis. On failing of normal distribution, implementation of non-parametric analysis were carried out using:
  Mann-Whitney Rank Sum
  One-way Anova
The data analysis were divided into six sections:
  Tumor Volume (The source data will be the measurements recorded on observation sheets. The tumor mass data required for the Hydration Value was sourced from animal autopsy sheets.)
  Starting Tumor Volume (Defined as the tumor volume (mm³) on the day treatment commenced (ie. Day 1).)
  Starting Tumor Volume as a Percentage of Net Body Weight (was calculated using the following formula:

$$\frac{\text{starting tumor volume (cm}^3\text{)} \times 100}{\text{body weight (g) on Day 1}}$$

Tumor Volume at Experimental end-point was defined as the tumor volume (mm³) on the day of death. For animals which are found dead the tumor volume measured at the last observation will be used.

Percentage Change in Tumor Volume at Experimental End-point—was calculated using the following formula:

$$\frac{\text{end-point tumor volume (mm}^3\text{)} - \text{starting tumor volume (mm}^3\text{)} \times 100}{\text{starting tumor volume (mm}^3\text{)}}$$

% T/C—was calculated using the following formula:

$$\frac{\text{\% change in tumor volume at experimental end-point of the Treatment group} \times 100}{\text{\% change in tumor volume at experimental end-point of the Control group}}$$

Classification of Tumor Progression

Following the completion of the study, mice from each treatment group were classified into one of four categories based on the extent of their tumor progression.

The categories and criteria for each were as follows (Maucher & von Angerer, *J Cancer Res Clin Oncol.* 120(8): 502-4.1994):

| | |
|---|---|
| Complete remission: | Tumor not palpable |
| Partial remission: | Tumor volume <50% of initial (equates to values <−50% change in tumor volume at experimental end-point) |
| Static Tumors: | Tumor volume 50-150% of initial (equates to values between −50 and 150% change in tumor volume at experimental end-point) |
| Progressing Tumors: | Tumor volume >150% of initial (equates to values >150% change in tumor volume at experimental end-point) |

Mean Tumor Volume

The mean tumor volume was calculated using the following formula:

$$\frac{\text{sum of the tumor volumes (mm}^3\text{) of each mouse}}{\text{number of mice}}$$

for each week of the treatment period and plotted ±SEM as a function of time.

Organ Mass

To investigate possible treatment induced organ atrophy or enlargement, the organs was removed and weighed during the post mortem.

The source data including the mouse and tumor masses were recorded where any animals found dead were not included in the data analysis.

The mass of each organ was calculated as a % of the net body weight at autopsy and compared to the organ masses of the saline only control group.

Body Mass

The source data was the measurements recorded. Any animals found dead were not included in the data analysis.

% Change in Net Body Mass at Experimental End-Point
Was calculated using the following formula:

$$\frac{[\text{end-point body mass } (ex \text{ tumor}) - \text{body mass at commencement of treatment } (ex \text{ tumor})] \times 100}{\text{body mass at commencement of treatment } (ex \text{ tumor})}$$

Mean % Change in Net Body Mass at Experimental End-Point
Was calculated using the following formula:

$$\frac{\text{sum of the \% change in net body mass at experimental end-point of each mouse}}{\text{number of mice}}$$

plotted ±SEM as a function of time.

Survival

The overall animal survival time was calculated as the time in days that the animal lived after the commencement of treatment which will be designated Day 1.

Monotherapy: Cetuximab as a Sole Therapy or Formulated with Hyaluronan

Monotherapy: Comparison of the Effectiveness of Cetuximab and HyERB: Tumor Volume The experimental end-point of the cetuximab, 0.25 and 0.5 mg/kg formulated with or without 150 mg/kg HA monotherapy regimen occurred at 120 days after the commencement of treatment. FIGS. 1A and B show the percentage change in tumor volume over time at different doses of cetuximab, 0.25 and 0.5 mg/kg, respectively.

Figure 1B:
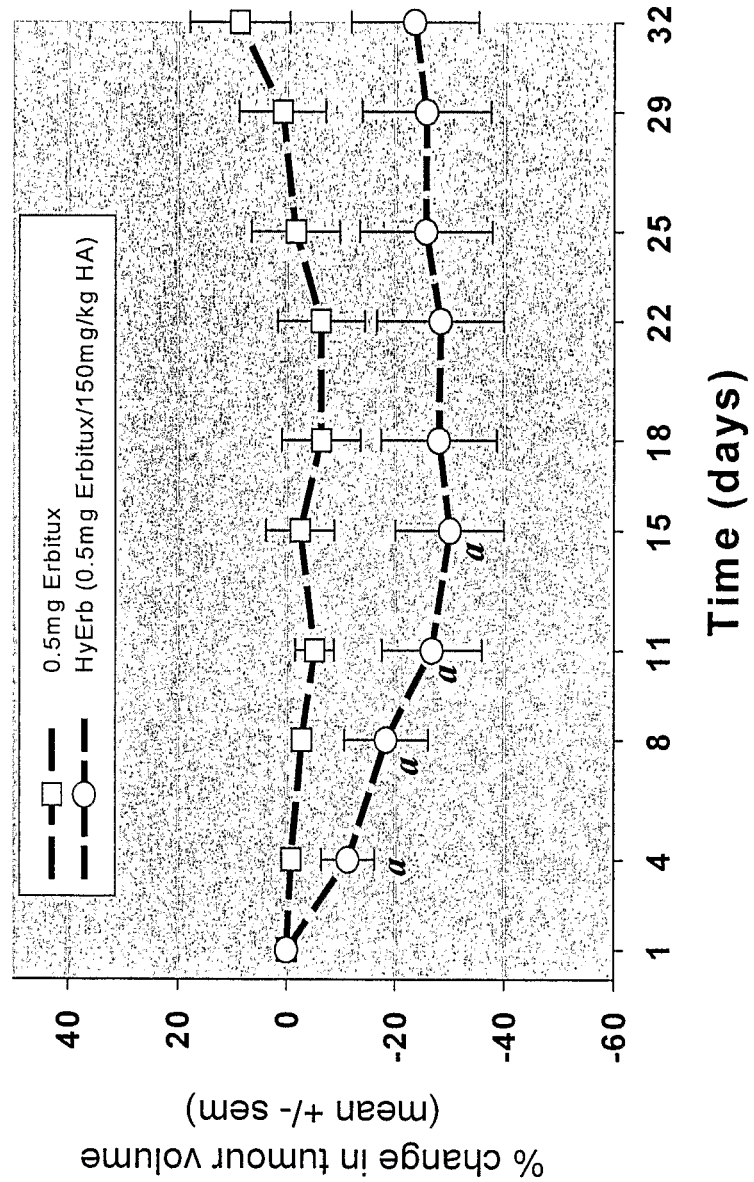
FIG. 1B demonstrates tumor response for ERB (0.5) and HyERB (150/0.5) during treatment (day 32). Points on graph marked 'a' denote the difference between treatment groups is statistically significant ($p=<0.05$, t-test).

Tumor response is dose dependant when comparing the cetuximab (0.25) and cetuximab (0.5) data. The formulation of cetuximab (0.25) with HA [HyERB(150/0.25)] did not demonstrate a significant difference in tumor response but when examining the tumor growth curves it became evident that the HyERB(150/0.25) resulted in slower tumor growth. Tumors treated with ERB(0.25) reached a 400% increase in tumor volume at Day 58 while animals treated with HyERB (150/0.25) reached an equivalent tumor size at Day 90 thereby resulting in a tumor growth delay of 32 days (35%). Mice receiving cetuximab (0.5) with HA tumors [HyERB (150/0.5)] demonstrated an even greater response where tumors were significantly smaller than the cetuximab (0.5) treatment group. HyERB(150/0.5) therapy caused a cytotoxic response (i.e. a reduction in tumor volume) over ERB(0.5) treatment (FIG. 1B), a response that has not been previously observed in therapeutic antibody studies. The difference in tumor response in the HyERB(150/0.5) versus ERB(0.5) treatment group was statistically significant up to day 15.

These data, therefore, demonstrate that formulating HA with cetuximab can increase the efficacy of the therapeutic antibody.

Monotherapy

Figure 2:
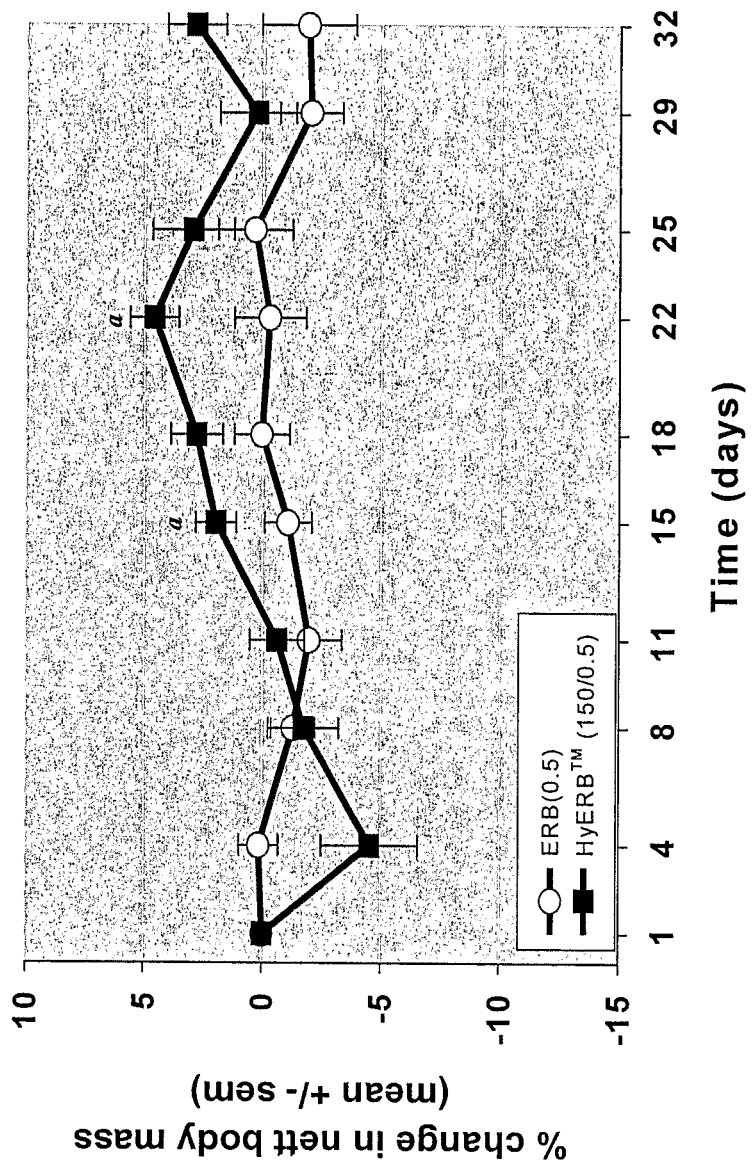
FIG. 2 is a graphical representation of % change in net body mass of the mice bearing human colon cancer xenografts where the mice are treated with hyaluronan formulated with cetuximab (HyERB) (150/0.5) or ERB (0.5) during treatment, day 32. Points on graph marked 'a' denote the difference between treatment groups is statistically significant ($p=<0.05$, t-test).

In preclinical studies, a loss of weight can often be an indicator of animal well-being and disease progression. Groups treated with ERB (0.5) and HyERB (150/0.5) are shown in FIG. 2. These data indicate that HyERB (150/0.5) treatment at days 15 and 22 are statistically higher than ERB (0.5) indicating the trend towards decreased disease progression when the antibody was formulated with HA.

Monotherapy: The Effect of Cetuximab on Survival

Figure 3:
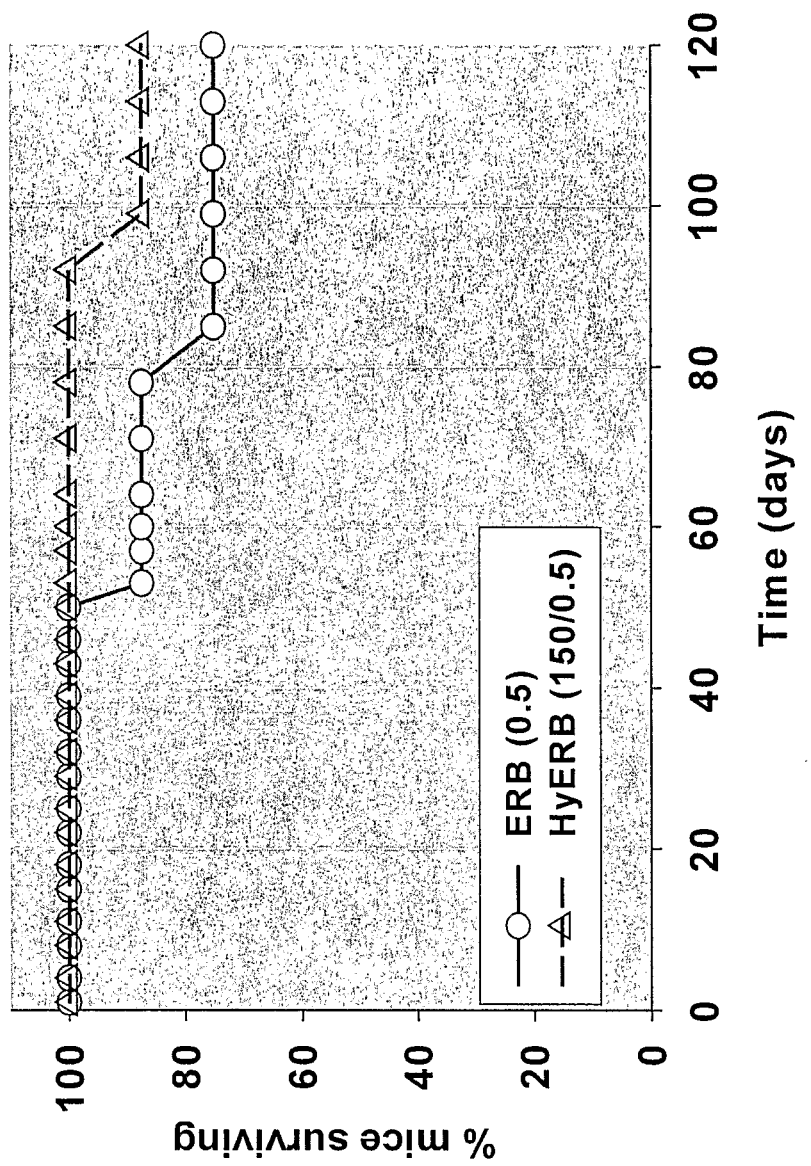
FIG. 3 is a graphical representation of % survival of mice bearing human colon cancer xenografts where the mice are treated with hyaluronan formulated with cetuximab (HyERB) (150/0.5) or ERB (0.5). Experimental endpoint was achieved at day 120 after the commencement of treatment where the % survival is expressed as the day of mouse death divided by $0.120 \times 100$. The survival data can be considered as a surrogate indicator of an increased therapeutic index.

Mouse survival data is shown in FIG. 3. For the HyERB (150/0.5) group one mouse was humanely killed on day 99 because the tumor volume was over 1000 mm$^3$. For the ERB (0.5) treatment group one mouse was humanely killed before the experimental endpoint on day 53 and one on day 85 because tumor volumes were 1000 mm$^3$. The remainder of the mice were killed due to completion of the treatment regimen. Increased survival due to a decrease in disease progression was observed for the HyERB group.

Combination therapy: HyERB (150/0.5)/HyCAMP (26.6/50) and ERB (0.5)/CAMP(50)

Figure 4A:
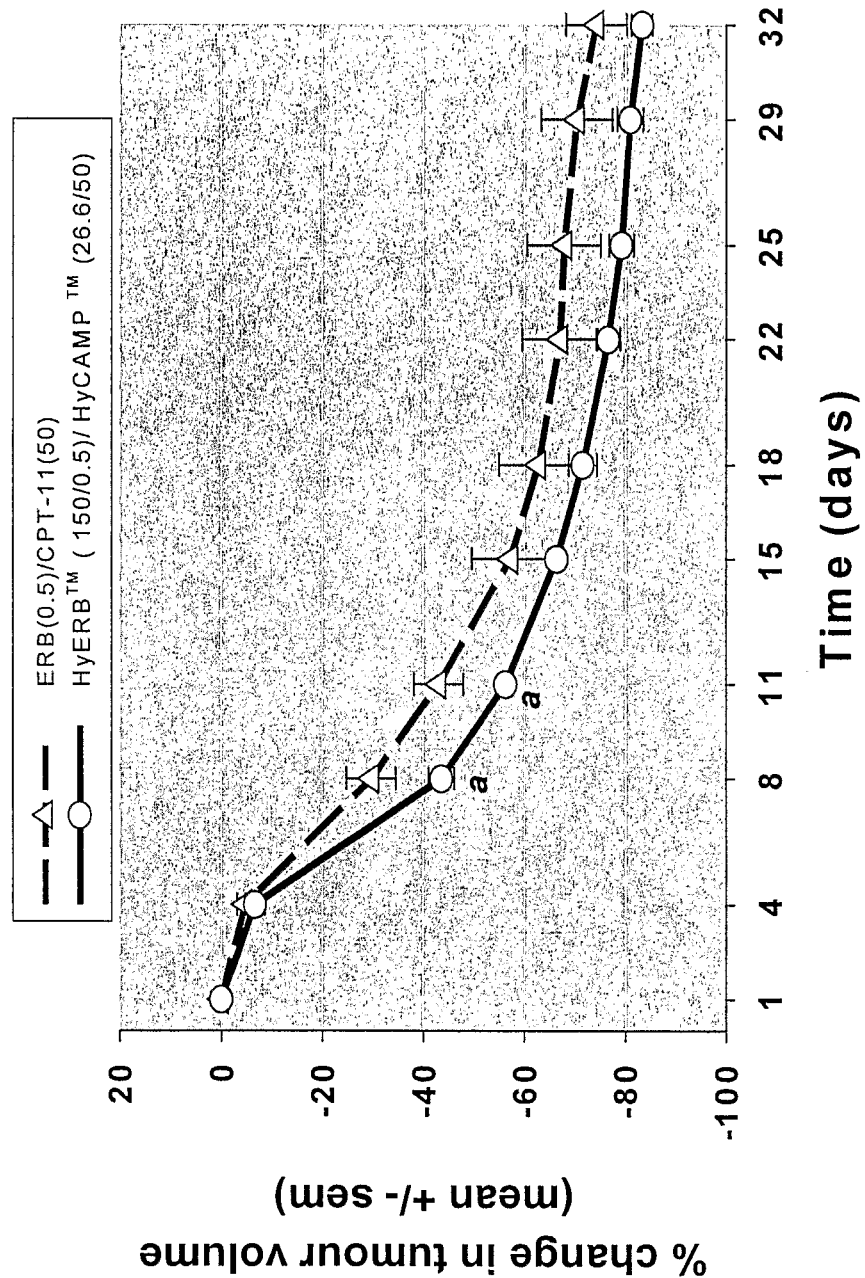
FIGS. 4A and B are a graphical representation of mice receiving the combination therapy, HA formulated with cetuximab (HyERB) with HA formulated with irinotecan (HyCAMP).
Figure 4B:
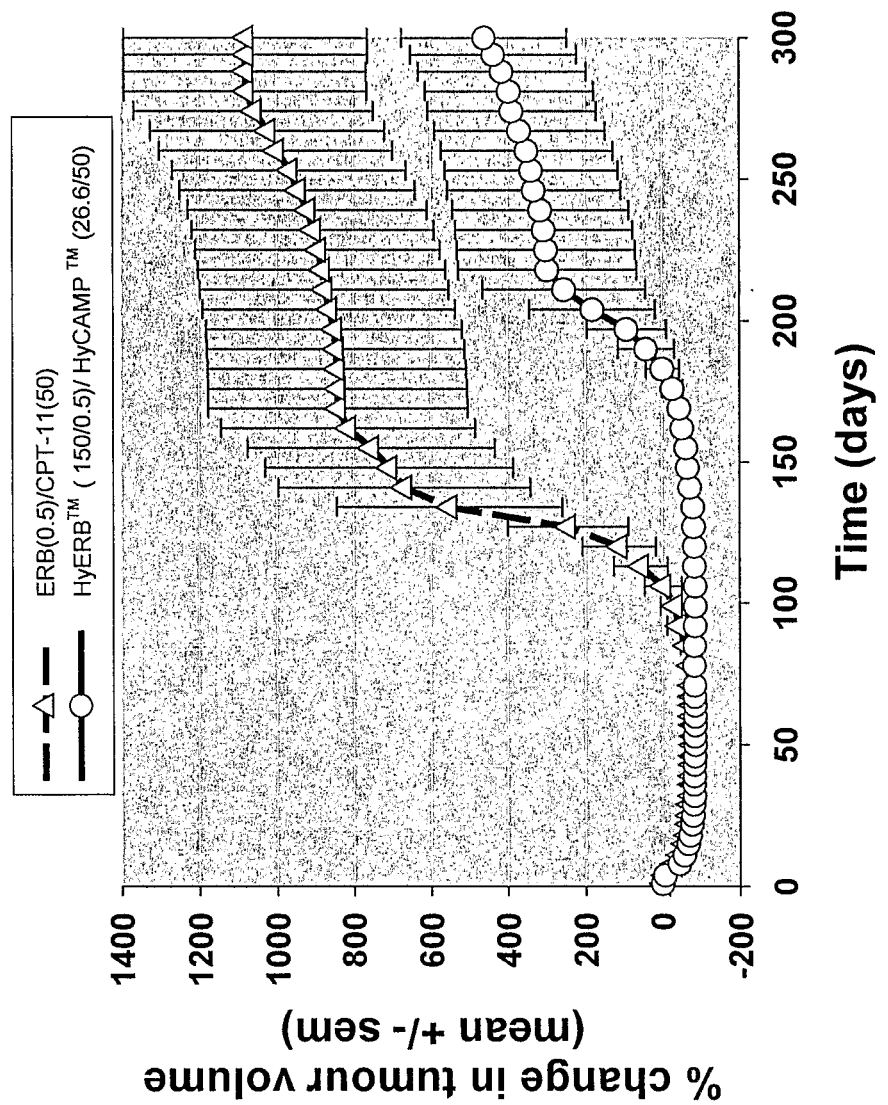
FIG. 4B shows the same experiment until experimental endpoint, day 300 after the commencement of treatment. Note: areas where the difference between groups is significant ($p=<0.05$, t-test) is denoted by 'a'.

Combination Therapy: Comparison of the Effectiveness of Combination Therapy on Tumor Volume FIGS. 4A and B show the percentage change in tumor volume for mice receiving the combination therapy, HA formulated with cetuximab with HA formulated with irinotecan (HyERB/HyCAMP), and cetuximab formulated with irinotecan (ERB/CPT-11). FIG. 4A shows the percentage change in tumor volume for the treatment up to day 32 (the day of the last injection). FIG. 4B shows the data to experimental end-point, day 300.

Mice receiving the combination therapy HyERB/HyCAMP display a significantly earlier tumor response when compared with the ERB/CAMP data (FIG. 4A). The vastly superior efficacy of the HyERB/HyCAMP combination over the time period to experimental endpoint, day 300, can bee seen in FIG. 4B where this is clearly indicated in the tumor growth curves. Animals treated with cetuximab/irinotecan (ERB/CAMP) demonstrated a mean increase in tumor volume of 600% by Day 135 while animals treated with HyERB/HyCAMP did not reach this degree of tumor growth, even at the experimental endpoint of 300 days.

Classification of Tumor Progression

Following the completion of the study, mice from each treatment group were classified into one of four categories based on the extent of their tumor progression as estimated from tumor volume data (Table 6).

At day 92, all tumors from both the saline and HA groups were classified as either static (12.5%) or progressing (87.5%).

Comparing between the monotherapy groups, HyERB with ERB treatment, showed that the addition of HA to the antibody cetuximab resulted in a significant shift in tumor progression toward partial and complete remission from day 92.

Comparing between combination therapy groups, HyERB/HyCAMP with ERB/CAMP, showed that when HA was present, there were no static or progressing tumors; all were in complete or partial remission. In contrast, for the ERB/CAMP treatment, at day 120 37.5% of tumors were progressing.

These data indicate that when HA is present in the formulation, tumor progress is altered towards remission. In conclusion, addition of HA to the combination therapy formulation significantly increased efficacy of the treatment.

Combination Therapy: Monitoring of Body Mass and Disease Progression

Figure 5:
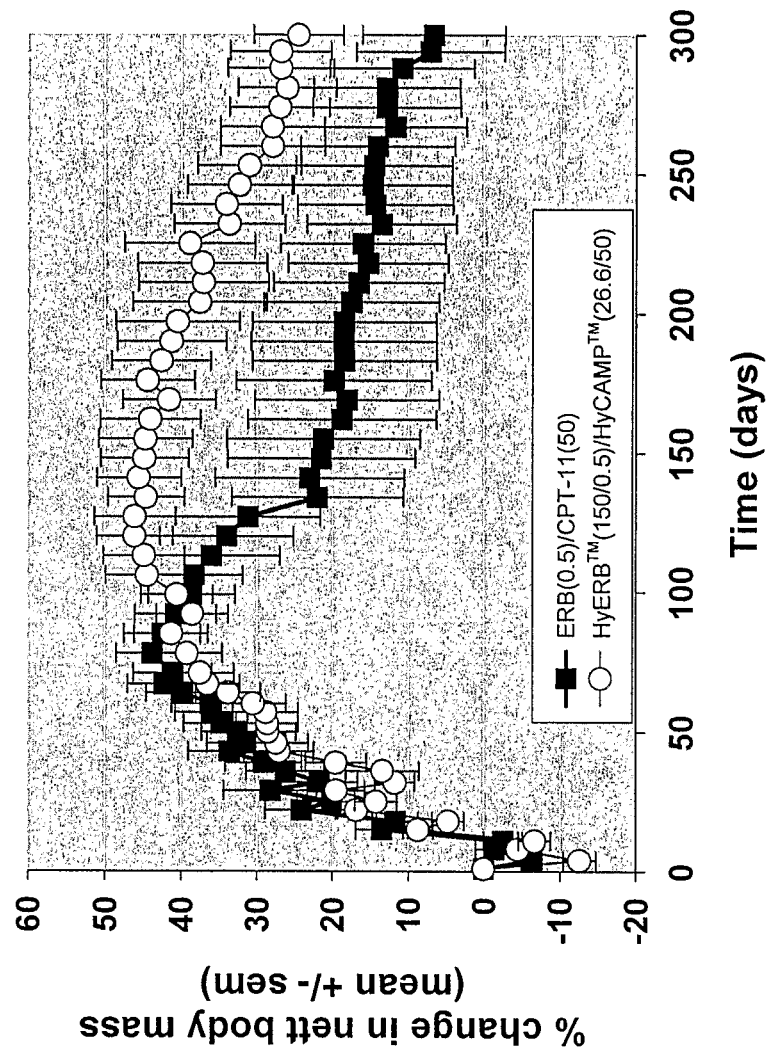
FIG. 5 is a graphical representation of % change in net body mass in combination therapy, HA formulated with cetuximab (HyERB) with HA formulated with irinotecan (HyCAMP) until the experimental endpoint, day 300 after the commencement of treatment.

Reduced weight loss translates to an increased animal benefit. Percentage change in net body mass in FIG. 5 indicates a reduced tumor burden for the HyERB/HyCAMP combination compared to ERB/CAMP. These data indicate that the addition of HA to the combination therapy formulation decreased disease progression.

Combination Therapy: Effect on Survival

Figure 6:
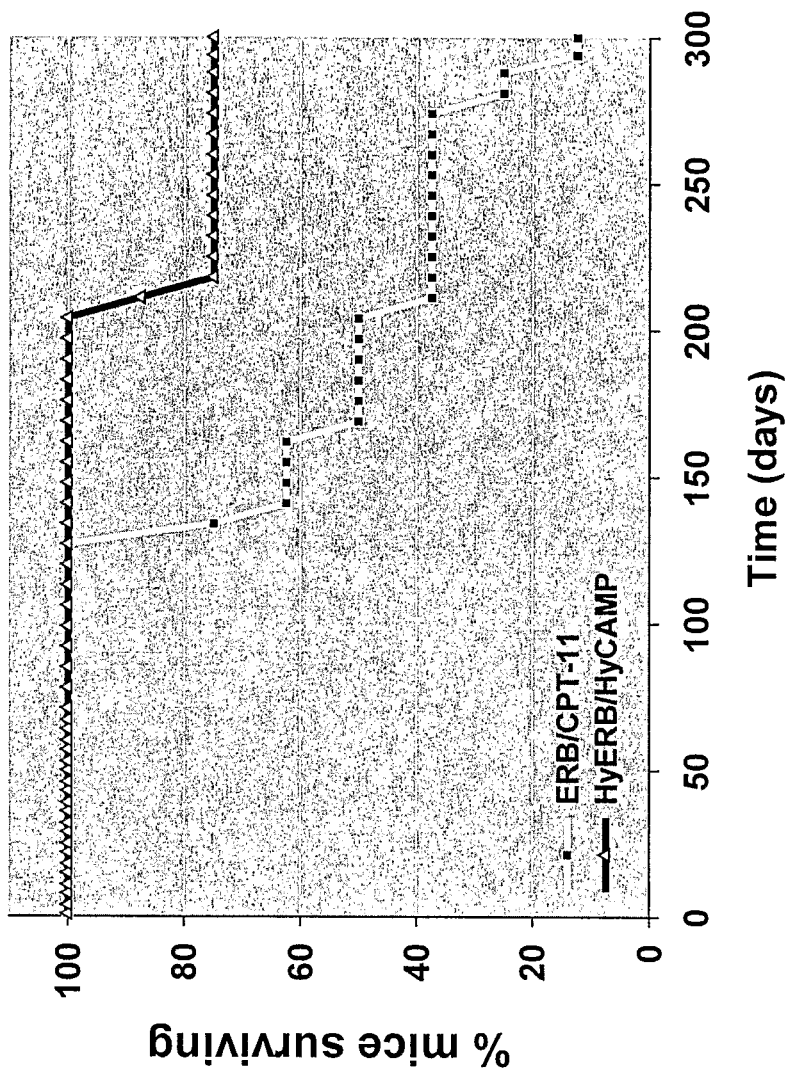
FIG. 6 is a graphical representation of the % mice surviving for the combination therapy, HA formulated with cetuximab (HyERB) with HA formulated with irinotecan (HyCAMP) until the experimental endpoint, day 300 after the commencement of treatment.

Most striking is the percentage of animals surviving when administered the HyERB/HyCAMP formulation when compared to the ERB/CAMP group (FIG. 6). For the HyERB/HyCAMP group, 6 mice survived until day 300 with one mouse being humanely killed at day 211 and 218 because the tumor volume was over 1000 mm$^3$. For the ERB/CAMP group only one mouse survived until day 300. Two mice were killed on day 134, one mouse on days 141, 169 and 281 because the tumor volume was over 1000 mm$^3$. On days 211 and 294 the mice were killed due to metabolic stress (i.e. weight loss).

TABLE 6

Classification of tumor progression in monotherapy and combination therapy treatment groups

| Test Compound | Day | Complete Remission$^a$ (%) | Partial Remission$^b$ (%) | Static Tumor$^c$ (%) | Progressing Tumor$^d$ (%) |
| --- | --- | --- | --- | --- | --- |
| Control: | 15 | 0 | 0 | 87.5 | 12.5 |
| Saline | 46 | 0 | 0 | 37.5 | 62.5 |
| | 71 | 0 | 0 | 25 | 75 |
| | 92 | 0 | 0 | 12.5 | 87.5 |
| | 106 | 0 | 0 | 0 | 100 |
| Control: | 15 | 0 | 0 | 50 | 50 |
| HA-only | 46 | 0 | 0 | 37.5 | 62.5 |
| | 71 | 0 | 0 | 37.5 | 62.5 |
| | 92 | 0 | 0 | 12.5 | 87.5 |
| | 120 | 0 | 0 | 0 | 100 |
| Monotherapy: | 15 | 0 | 25 | 75 | 0 |
| HyERB(150/0.5) | 46 | 0 | 37 | 63 | 0 |
| | 71 | 0 | 50 | 37 | 13 |
| | 92 | 12 | 37 | 37 | 13 |
| | 113 | 12 | 50 | 25 | 12 |
| | 120 | 25 | 37.5 | 0 | 37.5 |
| Monotherapy: | 15 | 0 | 0 | 100 | 0 |
| ERB(0.5) | 46 | 0 | 0 | 100 | 0 |
| | 71 | 0 | 0 | 86 | 14 |
| | 92 | 0 | 0 | 86 | 14 |
| | 113 | 0 | 0 | 86 | 14 |
| | 120 | 0 | 0 | 71.4 | 28.6 |
| Combination therapy: | 15 | 0 | 100 | 0 | 0 |
| HyERB/HyCAMP | 46 | 0 | 100 | 0 | 0 |
| | 71 | 12.5 | 87.5 | 0 | 0 |
| | 92 | 12.5 | 87.5 | 0 | 0 |
| | 113 | 12.5 | 87.5 | 0 | 0 |
| | 120 | 0 | 100 | 0 | 0 |
| Combination therapy: | 15 | 0 | 63 | 37 | 0 |
| ERB/CAMP | 46 | 12.5 | 75 | 12.5 | 0 |
| | 71 | 25 | 63 | 12.5 | 0 |
| | 92 | 25 | 37 | 37 | 0 |
| | 113 | 25 | 37 | 0 | 37 |
| | 120 | 25 | 37.5 | 0 | 37.5 |

EXAMPLE 5

Evaluation of the Effect of Hyaluronan on the Anti-Tumoral Properties of Bevacizumab (Avastin) in the Treatment of Human Colon Cancer Purpose of Study To evaluate the effect of hyaluronan on the efficacy of therapeutic doses of bevacizumab in the treatment of both colon cancer in nude mice as either monotherapy or in combination with irinotecan and/or leucovorin and/or 5-FU. Specific consideration of the follow efficacy parameters:
  Primary Tumor Volume
  Cancer Metastasis
  Treatment toxicity in relation to
    Body mass
    Organ mass
    Survival Materials and Methods Test and Control Articles The test articles and dosages which will be used in the study are as follows:
  Hyaluronic Acid (800-900 kD modal molecular weight); dosage 150 mg/kg
  Bevacizumab (Avastin; BEV); dosage 5.0 mg/kg
  Irinotecan Hydrochloride (Camptosar or CAMP); dosage 50 mg/kg
  Leucovorin; dosage 5 mg/kg
  5-Fluorouracil (5-FU); dosage 100 mg/kg
  HyBEV(150/0.5); these formulation comprise the components as 150 mg/kg HA & 0.5 mg/kg bevacizumab Treatment with (i) saline, (ii) HA, (iii) the formulation comprising HA with bevacizumab (HyBEV) (iv), bevacizumab (BEV), (v) HyBEV and irinotecan/leucovorin/5-FU (IFL) or (vi) BEV & irinotecan/leucovorin/5-FU (IFL) was commenced approximately 4-8 weeks after the tumor volume was in the range of 50-100 mm$^2$. Therapies were delivered by bolus IV on day 1 and 4 for a total of 5-weeks. Administration of irinotecan/leucovorin/5-FU (IFL) was day 1 of a 7-day cycle for a total of 5-weeks. Mice were observed for 120-days for tumor re-growth. Table 7 provides the dosage components and the mean tumor volume of each treatment group at commencement of treatment.

TABLE 7

Tumor volume at commencement of treatment

| Treatment Group* | Dosage of components in first formulation per animal (mg/kg) | | Dosage of components in the second, (IFL formulation) per animal (mg/kg)# | | | Tumor volume (mm³) Mean ± SD | |
|---|---|---|---|---|---|---|---|
| | HA | bevacizumab | irinotecan | leucovorin | 5FU | at commencement of treatment | as percentage of body mass at commencement of treatment |
| Control: IFL + Saline | — | — | — | — | — | 79.54 ± 8.2 | 0.46 ± 0.07 |
| Combination therapy: IFL + HyBEV | 150 | 5.0 | 50 | 5 | 100 | 81.82 ± 9.53 | 0.51 ± 0.05 |
| Combination therapy: IFL + HyBEV | — | 5.0 | 50 | 5 | 100 | 76.99 ± 7.27 | 0.48 ± 0.09 |

*8 animals per treatment group.
Note after one cycle of IFL chemotherapy dose reduction of 5-FU from 100- to 50 mg/kg was undertaken due to excessive weightloss in both treatment arms. Remaining four cycles are 50 mg/kg 5-FU.

Administration of Drugs and Control Vehicles

The mice were randomly distributed into each of six treatment groups (n=8 per group). Individual mice were placed in an injection box and treatment administration was via the tail vein using a 26-gauge needle. To ensure the accuracy of each administered dosage, syringes were weighed before and after injection using an analytical; four decimal place balance.

The administration schedule for each group is listed in Table 8.

TABLE 8

Treatment administration protocol

| Treatment Group* | Dosage of components in first formulation per animal (mg/kg) | | Dosage of components in second formulation per animal (mg/kg) | | | Administration Protocol |
|---|---|---|---|---|---|---|
| | HA | bevacizumab | irinotecan | leucovorin | 5FU | |
| Control: IFL + saline | — | — | — | — | — | Day 1, 4 × 5 weeks |
| Combination therapy: HyBEV with IFL | 150 | 5.0 | 50 | 5 | 100 | Day 1, 4 × 5 weeks Day 1 × 5 weeks |
| Combination therapy: BEV with IFL | — | 5.0 | 50 | 5 | 100 | Day 1, 4 × 5 weeks Day 1 × 5 weeks |

*n = 8 per group

A sterile stock of Bevacizumab (Avastin) was purchased as a single vial containing 100 mg in a final volume of 4 mL (25 mg/mL).

Individual injections were prepared according to individual mouse masses, with the aim of delivering 50 mg/kg irinotecan (equivalent to human therapeutic dose of 208 mg/m²; MIMS1999). 10 mg/mL solution was prepared from batches of desiccated hyaluronan (HA) and packaged into single use 100 mL sterile glass vials. Hyaluronan combined with Bevacizumab (HyBEV) was prepared by mixing a portion of 25 mg/mL stock bevacizumab with the HA solution to a final HA concentration of 150 mg/kg of mouse mass and 0.5 mg/kg bevacizumab.

Solutions, formulations and administration for IFL treatment (i.e irinotecan and leucovorin and 5FU) where administered in a standard manner know in the art.

The treatments were quantitatively administered via the tail vein.

Figure 7:
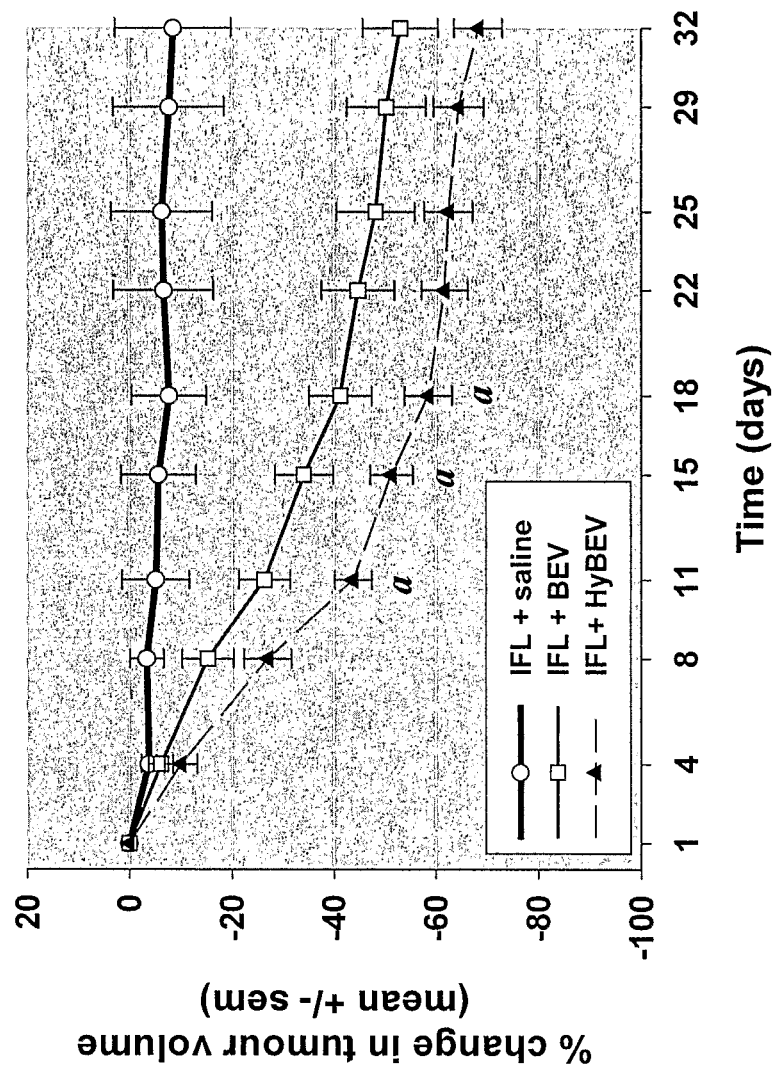
FIG. 7 is a graphical representation illustrating the percent change in tumor volume during the treatment of the mice until the end of treatment (day 32) after the commencement of treatment with irinotecan/5-fluorouracil/leucovorin (IFL+saline), IFL+bevacizumab (BEV) and IFL+HyBEV (HA formulated with bevacizumab). 'a' denotes the difference between IFL+BEV and IFL+HyBEV response is significant ($p=<0.05$, t-test).

For all other materials, methods and calculation used for this study, see as for Example 4. This includes:

Human Colon Carcinoma Cell Line
Mouse Tumor Model
Animal Maintenance and Housing
Monitoring of body mass, tumor volume and animal well being
Killing of animals at experimental end-point
Collection and processing of tumor and body organs
Analysis of Data
Classification of Tumor Progression
Mean Tumor Volume
Organ Mass
Body Mass
% change in net body mass at experimental end-point
Mean % change in net body mass at experimental end-point
Survival
Results and Conclusions
IFL with Bevacizumab in the LIM1215 Xenograph Model: Tumor Volume FIG. 7 show the percentage change in tumor volume for mice receiving the combination therapy IFL+BEV and IFL+HyBEV. The inclusion of HyBEV with the IFL regimen results in significantly earlier tumor response (a: $p<0.05$) when compared with the IFL+BEV treatment group. These data demonstrate that the addition of HA to the antibody enhances efficacy.

Classification of Tumor Progression

At experimental endpoint (134 days) tumors were classified into one of four categories based on the extent of their tumor progression as estimated from tumor volume data according to Maucher & von Angerer, 1994 supra. This data is presented in Table 9.

TABLE 9

Tumor classification at 4, 15, 32, 46, 71, 92 and 134 days in LIM1215 colon cancer xenografts receiving IFL + saline, IFL + BEV and IFL + HyBEV

| | Complete Remission (% of mice) | | | Partial Remission (% of mice) | | | Static Tumor (% of mice) | | | Progressing Tumor (% of mice) | | |
|---|---|---|---|---|---|---|---|---|---|---|---|---|
| | Treatment* | | | | | | | | | | | |
| Day | IFL + saline | IFL + BEV | IFL + HyBEV | IFL + saline | IFL + BEV | IFL + HyBEV | IFL + saline | IFL + BEV | IFL + HyBEV | IFL + saline | IFL + BEV | IFL + HyBEV |
| 4 | — | — | — | — | — | — | 100 | 100 | 100 | — | — | — |
| 15 | — | — | — | — | 12.5 | 62.5 | 100 | 87.5 | 37.5 | — | — | — |
| 32# | — | — | — | — | 62.5 | 87.5 | 100 | 37.5 | 12.5 | — | — | — |
| 46 | — | — | — | — | 75 | 87.5 | 100 | 25 | 12.5 | — | — | — |
| 71 | — | — | — | — | 50 | 87.5 | 50 | 37.5 | 12.5 | 50 | — | 12.5 |
| 92 | — | — | 12.5 | — | 37.5 | 75 | 16.7 | 37.5 | — | 83.3 | 12.5 | 25 |
| 134 | — | — | 12.5 | — | 12.5 | 37.5 | — | 50 | 12.5 | 100 | 25 | 37.5 |

*IFL + saline (n = 6); IFL + BEV (n = 8); IFL + HyBEV (n = 8)
Last day of treatment The data show that IFL+saline holds tumors static until day 71, however, by day 134 all tumor are progressing.

Comparing the groups, IFL+BEV with the IFL+HyBEV at day 92, shows that the addition of HA to the treatment resulted in a shift in tumor progression toward partial and complete remission. Indicating that HA increases efficacy.

Gastro-Intestinal Toxicity: Monitoring of Body Mass

Figure 8:
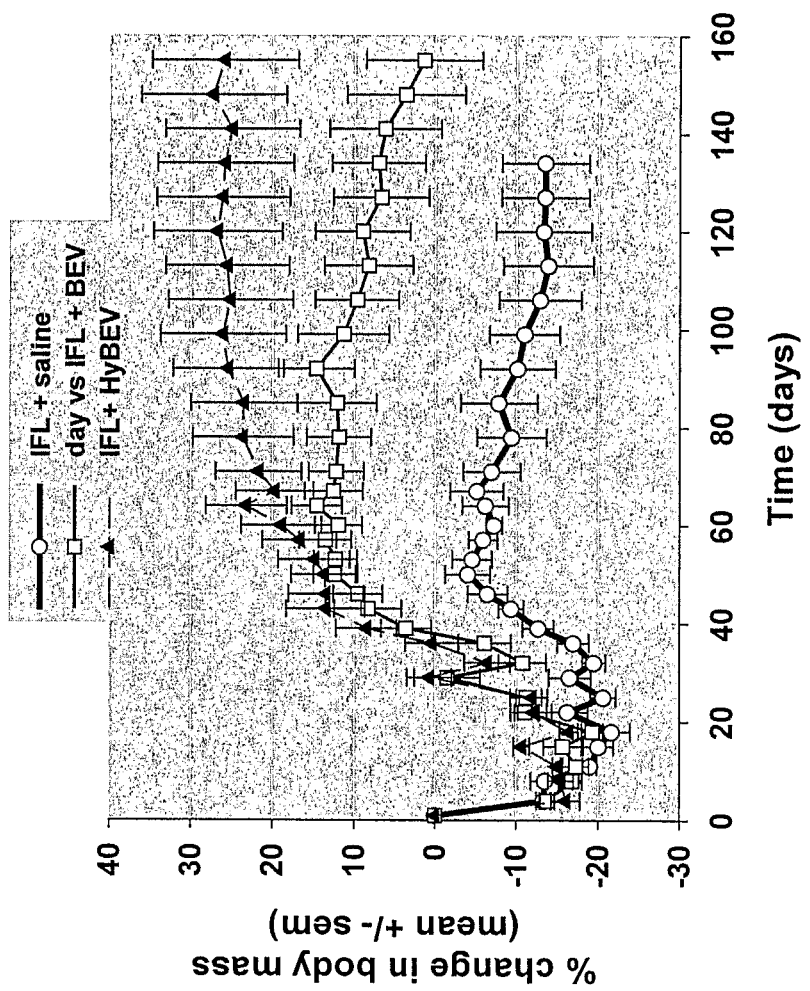
FIG. 8 is a graphical representation of % change in net body mass for 1 after the commencement of treatment with irinotecan/5-fluorouracil/leucovorin (IFL+saline), IFL+bevacizumab (BEV) and IFL+HyBEV (HA formulated with bevacizumab). The difference between the IFL+saline group is significant from day 25 to 134 when compared to IFL+BEV and IFL+HyBEV. For the same period although a trend is observed where weight gain is better for mice receiving IFL+HyBEV when compared with those receiving IFL+BEV, these differences are not significant.

Percentage change in net body mass in FIG. 8 shows the difference between the IFL+saline group is significant from day 25 to 134 when compared to IFL+BEV and IFL+HyBEV groups. For the same period although a trend is observed where weight gain is better for mice receiving IFL+HyBEV when compared with those receiving IFL+BEV, these differences are not significant. The trends show that HyBEV increase animal wellbeing. These data suggest that HA is having an effect on the gastrointestinal tract by reducing toxicity, a known toxicity of bevacizumab.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

European Patent No. 0 265 116
European Patent No. 0 138 572
Goodman and Gilman's *The Pharmacological Basis for Therapeutics* (7th ed.)
Langer, *Science* 249: 1527, 1990
Maucher & von Angerer, *J Cancer Res Clin Oncol.* 120(8): 502-4, 1994
MIMS annual, 1999
Remington's Pharmaceutical Sciences, 15th ed. Easton: Mack Publishing Co.: 1405-1412, 1461-1487, 1975
The National Formulary XIV., 14th ed. Washington: American Pharmaceutical Association, 1975
U.S. Pat. No. 4,160,452
U.S. Pat. No. 4,256,108
U.S. Pat. No. 4,265,874
U.S. Pat. No. 4,851,521
U.S. Pat. No. 4,965,353
U.S. Pat. No. 4,965,353
U.S. Pat. No. 5,208,020
U.S. Pat. No. 5,202,431
U.S. Pat. No. 5,475,092
U.S. Pat. No. 5,585,499
U.S. Pat. No. 5,676,964
U.S. Pat. No. 5,846,545
U.S. Pat. No. 6,620,927
U.S. Pat. No. 6,579,978
U.S. Pat. No. 6,831,172

The invention claimed is:

1. A formulation comprising hyaluronan (HA), or salt thereof, wherein the hyaluronan is in the molecular weight range of about 800 kDaltons to 900 kDaltons, and a therapeutic antibody selected from the group of antibodies consisting of: Bevacizumab; Cetuximab and Rituximab, or antigen-binding portion thereof and, optionally, one or more, pharmaceutically acceptable carriers, diluents and/or excipients, and
    wherein the hyaluronan or synthesized form thereof and the therapeutic antibody are not covalently bound; and
    wherein said formulation does not comprise a non-antibody chemotherapeutic agent.

2. The formulation of claim 1, wherein the hyaluronan has a modal molecular weight of 860 kDaltons.

3. The formulation of claim 1, wherein the pH range of the composition is between pH 2.5 and 10.5.

4. The formulation of claim 1, wherein the pH range of the composition is between pH 5.0 and 8.5.

5. The formulation of claim 1, wherein the therapeutic antibody is cetuximab.

6. The formulation of claim 1, wherein the therapeutic antibody is bevacizumab.

7. The formulation of claim 1, wherein the therapeutic antibody is humanised.

8. The formulation of claim 1, wherein the composition is in parenteral form.

9. The formulation of claim 8, wherein the parenteral form is formulated for subcutaneous injection, intravenous, intramuscular, intrathecal, intracranial, intrasternal injection or infusion techniques.

10. The formulation of claim 1, wherein the HA is administered in an amount of about 0.01 to about 40 mg/kg of body weight.

11. The formulation of claim 1, wherein the HA is administered in an amount of about 0.1 to about 27 mg/kg of body weight.

12. A formulation comprising an aqueous suspension of hyaluronan (HA), or salt thereof, wherein the hyaluronan is in the molecular weight range of about 800 kDaltons to 900 kDaltons, in admixture with a therapeutic antibody selected from the group of antibodies consisting of: Bevacizumab; Cetuximab and Rituximab, or antigen-binding portion thereof and one or more, pharmaceutically acceptable carriers, diluents and/or excipients; wherein said formulation does not comprise a non-antibody chemotherapeutic agent.

13. The formulation of claim 12, wherein the hyaluronan has a modal molecular weight range of 860 kDaltons.

14. The formulation of claim 12, wherein the therapeutic antibody is cetuximab.

* * * * *

UNITED STATES PATENT AND TRADEMARK OFFICE
CERTIFICATE OF CORRECTION

| | |
|---|---|
| PATENT NO. | : 8,623,354 B2 |
| APPLICATION NO. | : 12/065945 |
| DATED | : January 7, 2014 |
| INVENTOR(S) | : Tracey J. Brown et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 500 days.

Signed and Sealed this
Twenty-ninth Day of September, 2015

Michelle K. Lee
*Director of the United States Patent and Trademark Office*